US007919234B2

(12) United States Patent
Mulvey et al.

(10) Patent No.: US 7,919,234 B2
(45) Date of Patent: Apr. 5, 2011

(54) METHODS AND COMPOSITIONS FOR DETERMINING THE PATHOGENIC STATUS OF INFECTIOUS AGENTS

(75) Inventors: Matthew C. Mulvey, Baltimore, MD (US); Leo Einck, McLean, VA (US); Katherine Sacksteder, Baltimore, MD (US)

(73) Assignee: Sequella, Inc., Rockville, MD (US)

( * ) Notice: Subject to any disclaimer, the term of this patent is extended or adjusted under 35 U.S.C. 154(b) by 0 days.

(21) Appl. No.: 12/080,929

(22) Filed: Apr. 7, 2008

(65) Prior Publication Data

US 2009/0047658 A1 Feb. 19, 2009

Related U.S. Application Data

(60) Provisional application No. 60/922,213, filed on Apr. 5, 2007, provisional application No. 60/927,287, filed on May 1, 2007, provisional application No. 60/927,217, filed on May 2, 2007.

(51) Int. Cl.

| | |
|---|---|
| ***C12Q 1/02*** | (2006.01) |
| ***C12Q 1/68*** | (2006.01) |
| ***C12Q 1/70*** | (2006.01) |

(52) U.S. Cl. ................................... 435/5; 435/6; 435/29

(58) Field of Classification Search ......................... None
See application file for complete search history.

(56) References Cited

U.S. PATENT DOCUMENTS

| | | | | |
|---|---|---|---|---|
| 5,478,727 | A * | 12/1995 | Roizman et al. | 435/23 |
| 6,300,061 | B1 | 10/2001 | Jacobs, Jr. et al. | |
| 2002/0156016 | A1* | 10/2002 | Minuk | 514/12 |

OTHER PUBLICATIONS

Drug Resistance Threatens to Reverse Medical Progress, www.who.int—*Press Release*, pp. 1-4, Jun. 12, 2000.

PCT/US08/04491—International Search Report, *PCT—International Search Report*, pp. 1-8, Jun. 20, 2008.

Dye et al., Consensus Statement, Global Burden of Tuberculosis: Estimated Incidence, Prevalence, and Mortality by County. WHO Global Surveillance and Monitoring Project, *Journal of the American Medical Association*, vol./Iss: 282 (7), pp. 677-686, Aug. 18, 1999.

Lewis, R., The Rise of Antibiotic-Resistant Infections, *online*—www.fda.gov, pp. 1-7, Sep. 1, 1995.

* cited by examiner

*Primary Examiner* — Mark Navarro
(74) *Attorney, Agent, or Firm* — Johnson & Associates

(57) ABSTRACT

Methods and compositions for the detection of disease caused by infectious agents and microbes are provided. In particular, methods and compositions comprising novel combinations of nucleic acid amplification and drug susceptibility technologies are provided. In certain embodiments, the present invention enables the detection of infectious agents and microbes as well as providing information concerning the viability status of the agent or microbe. In one embodiment, the present invention is used for the detection of mycobacterial infections, including, but not limited to, tuberculosis.

27 Claims, 9 Drawing Sheets

METHODS AND COMPOSITIONS FOR DETERMINING THE PATHOGENIC STATUS OF INFECTIOUS AGENTS

CROSS REFERENCE TO RELATED PATENT APPLICATIONS

The present application claims priority to U.S. Provisional Patent Application Ser. No. 60/922,213, filed Apr. 5, 2007, U.S. Provisional Patent Application Ser. No. 60/927,287, filed May 1, 2007 and U.S. Provisional Patent Application Ser. No. 60/927,217, filed May 2, 2007.

FIELD OF INVENTION

The present invention relates to methods and compositions for improved diagnosis of infectious disease. In particular, the present invention provides novel methods for detecting infectious agents, providing information about the viability status of such infectious agents and for determining drug susceptibility. In certain embodiments, the present invention employs techniques involving nucleic acid amplification-based microbial identification together with phage-based biological detection of drug resistance. The methods of the invention are suitable for all infectious agents and microbes, including bacterial agents such as mycobacteria.

BACKGROUND OF THE INVENTION

When penicillin became widely available during the second world war, it was a medical miracle, rapidly vanquishing the biggest wartime killer—infected wounds. Discovered initially by a French medical student, Ernest Duchesne, in 1896, and then rediscovered by Scottish physician Alexander Fleming in 1928, the product of the soil mold *Penicillium* crippled many types of disease-causing bacteria. But just four years after drug companies began mass-producing penicillin in 1943, microbes began appearing that could resist it.

The first bug to battle penicillin was *Staphylococcus aureus*. This bacterium is often a harmless passenger in the human body, but it can cause illness, such as pneumonia or toxic shock syndrome, when it overgrows or produces a toxin. In 1967, another type of penicillin-resistant pneumonia, caused by *Streptococcus pneumoniae* and called pneumococcus, surfaced in a remote village in Papua New Guinea. At about the same time, American military personnel in Southeast Asia were acquiring penicillin-resistant gonorrhea from prostitutes. By 1976, when the soldiers had come home, they brought the new strain of gonorrhea with them, and physicians had to find new drugs to treat it. In 1983, a hospital-acquired intestinal infection caused by the bacterium *Enterococcus faecium* joined the list of bugs that outwit penicillin.

Antibiotic resistance spreads fast. Between 1979 and 1987, for example, only 0.02 percent of pneumococcus strains infecting a large number of patients surveyed by the National Centers for Disease Control and Prevention (CDC) were penicillin-resistant. The CDC's survey included 13 hospitals in 12 states. By 1994, 6.6 percent of pneumococcus strains were resistant, according to a report in the Jun. 15, 1994, Journal of the American Medical Association by Robert F. Breiman, M.D., and colleagues at CDC. The agency also reports that in 1992, 13,300 hospital patients died of bacterial infections that were resistant to antibiotic treatment. (R. Lewis "The Rise of Antibiotic-Resistant Infections" www.fda.gov).

According to experts in the field such as Michael Blum, M.D. (medical officer in the Food and Drug Administration's division of anti-infective drug products), one of the main contributors of the alarming increase in antibiotic-resistant infections was a result of complacency: "There was complacency in the 1980s. The perception was that we had licked the bacterial infection problem. Drug companies weren't working on new agents. They were concentrating on other areas, such as viral infections. In the meantime, resistance increased to a number of commonly used antibiotics, possibly related to overuse of antibiotics. In the 1990s, we've come to a point for certain infections that we don't have agents available." According to a report in the Apr. 28, 1994, New England Journal of Medicine, researchers have identified bacteria in patient samples that resist all currently available antibiotic drugs.

The increased prevalence of antibiotic resistance is an outcome of evolution. Any population of organisms, bacteria included, naturally includes variants with unusual traits—in this case, the ability to withstand an antibiotic's attack on a microbe. When a person takes an antibiotic, the drug kills the defenseless bacteria, leaving behind—or "selecting," in biological terms—those that can resist it. These renegade bacteria then multiply, increasing their numbers a millionfold in a day, becoming the predominant microorganism.

The antibiotic does not technically cause the resistance, but allows it to happen by creating a situation where an already existing variant can flourish. "Whenever antibiotics are used, there is selective pressure for resistance to occur. It builds upon itself. More and more organisms develop resistance to more and more drugs," says Joe Cranston, Ph.D., Director of the Department of Drug Policy and Standards at the American Medical Association in Chicago.

A patient can develop a drug-resistant infection either by contracting a resistant bug to begin with, or by having a resistant microbe emerge in the body once antibiotic treatment begins. Drug-resistant infections increase risk of death, and are often associated with prolonged hospital stays, and sometimes complications. These might necessitate removing part of a ravaged lung, or replacing a damaged heart valve.

Disease-causing microbes thwart antibiotics by interfering with their mechanism of action. For example, penicillin kills bacteria by attaching to their cell walls, then destroying a key part of the wall. The wall falls apart, and the bacterium dies. Resistant microbes, however, either alter their cell walls so penicillin can't bind or produce enzymes that dismantle the antibiotic.

In another scenario, erythromycin attacks ribosomes, structures within a cell that enable it to make proteins. Resistant bacteria have slightly altered ribosomes to which the drug cannot bind. The ribosomal route is also how bacteria become resistant to the antibiotics tetracycline, streptomycin and gentamicin.

Tuberculosis is an infection that has experienced spectacular ups and downs. Drugs were developed to treat it, complacency set in that it was beaten, and the disease resurged because patients stopped their medication too soon and infected others. Today, one in seven new tuberculosis cases is resistant to the two drugs most commonly used to treat it (isoniazid and rifampicin), and 5 percent of these patients die. Two billion people are infected with *Mycobacterium tuberculosis* (Mtb), leading to 8 million new tuberculosis cases each year and nearly three million resultant deaths. A considerable obstacle to tuberculosis control is the emergence of drug-resistant disease. A median of 9.9% of Mtb strains isolated from patients with no history of prior treatment are resistant to at least one front-line antitubercular (anti-tuberculosis) drug. Multidrug-resistant strains of tuberculosis (MDR-tuberculosis), defined as resistant to at least isoniazid (INH) and rifampicin (RIF), persist in approximately 50 million people worldwide, resulting in nearly 500,000 new cases of MDR-TB each year. MDR-TB is much more difficult and expensive than drug-susceptible tuberculosis to treat, for it requires up to two years of therapy with a combination of drugs, including second-line drugs that are less potent and more toxic than the first-line therapies. Recent studies document the disturbing incidence and global distribution of extensively drug-resistant tuberculosis (XDR-tuberculosis), defined as MDR-TB strains additionally resistant to any fluoroquinolone, and at least one of three injectable second-line antibiotics. The emergence of MDR and especially XDR-TB threaten to return tuberculosis care and control to the pre-antibiotic era.

Key to stemming the spread of drug-resistant tuberculosis is the development of rapid and accurate diagnostics to identify M/XDR-TB infection. Gold-standard antibiotic susceptibility tests (AST) require several weeks or months to perform because they measure the growth of this notoriously slow-growing bacteria. Regardless of the time required for conducting the AST tests, these techniques remain important and valuable as they are very accurate because they biologically measure the effect an antimicrobial has on a tuberculosis isolate.

Traditional methods to identify drug resistant strains of Mtb involve culturing Mtb isolated from clinical specimens in either liquid culture or on solid supports such as LJ slants or agar plates supplemented with the appropriate nutrient media for growth of mycobacteria. After the culture reaches a sufficient population density allowing visual identification of bacterial growth either by an increase in turbidity of a liquid culture or by colony formation on LJ slants or agar plates, the isolate is sub-cultured into two or more individual vessels either containing a different antibiotic or none at all. The effect of the antibiotic on the Mtb isolate is determined by comparing the growth of the antibiotic-containing subculture to one in which no drug was added. If the Mtb isolate is susceptible to the antibiotic, it will not grow sufficiently compared to the control. However, if the strain is resistant to the anti-tuberculosis drug, then it will continue to grow as it has the ability to circumvent the antimicrobial properties of the antibiotic. Second-generation versions of this biological, growth-based assay speed the time to detection of both microbial identification as well as resistance testing by using radiometric (e.g. Becton Dickinson's BACTEC™) or calorimetric (e.g. Becton Dickinson's MGIT™ and Biomerieux's BACT ALERT®) devices to measure metabolic products produced by growing Mtb, rather than waiting for the bacterial population to reach a density sufficient to be seen by the naked eye.

More recent approaches to speed the biological detection of drug resistance in Mtb have focused on using mycobacteriophage to probe the effect an anti-microbial has on an Mtb isolate. Mycobacteriophage are viruses that infect *Mycobacteria* and hijack cellular biosynthetic machines to replicate and spread. Broadly speaking, viruses are obligate intracellular parasites: they rely on the biosynthetic machinery of the host cell to manufacture progeny in order to reproduce and spread. The extent to which an infecting virus is able to direct the synthesis and production of new viral components is largely dictated by the metabolic capacity (i.e. the viability status) of the host cell. In the extreme version, a living cell, which is metabolically active, can be infected by a virus and be co-opted for the production of new virus while a dead, metabolically inactive cell, cannot. Therefore, the extent to which a virus is able to infect and replicate in a host cell indicates the metabolic capacity of that cell. Because antibiotics ultimately affect the metabolic capacity of a susceptible bacterial cell, and phage hijack the biosynthetic machines of the host, antibiotics also have an effect on the replication and spread of bacteriophage. Furthermore, phage are able to find and infect small numbers of bacteria and because they replicate and spread so much faster than the host cell, especially in the case of Mtb, they can be used to dramatically speed the detection and AST of Mtb.

Biotec, Inc.'s (Suffolk, United Kingdom) product FAST-PLAQUE-RESPONSE™ measures the ability of the mycobacteriophage D29 to replicate inside Mtb after exposure to antibiotics. Mtb isolated from a clinical specimen are split into two vessels: one contains the anti-microbial rifampicin while the other contains no antibiotic and serves as a positive control. After rifampicin is given sufficient time to exert its effects on Mtb, D29 is added to both tubes and given sufficient time to inject its DNA into Mtb and hijack the cell to make progeny virus. Prior to lysis of Mtb by phage-encoded lysis functions, extracellular phage that did not infect Mtb are killed by addition of a chemical virucide, which cannot penetrate inside Mtb and therefore kills all extra-cellular phage. The virucide and antibiotic are then removed and a fast-growing mycobacteria, *M. smegmatis* (Msmeg), is added to the phage-infected Mtb. The mixture is then plated onto agar dishes. Because Msmeg replicates quickly, a bacterial lawn is formed on the agar plates after overnight incubation at 37° C. Furthermore, Msmeg is efficiently infected by D29, which forms clear and visible plaques on Msmeg bacterial lawns. Each plaque represents an Mtb cell that was initially infected by D29 and produced progeny phage. This assay quantitatively measures D29 replication in small numbers of Mtb. Furthermore, because phage replication is wholly dependent upon the metabolic capacity of the host cell, quantitative measurements of D29 replication in Mtb exposed to an anti-microbial compared to an untreated control accurately measures the extent to which that antibiotic can disrupt Mtb metabolism, and ultimately bacterial growth. Low viral replication reflects antibiotic-mediated inhibition of cellular metabolism, whereas high viral replication biologically demonstrates Mtb drug resistance. Finally, this phage-based drug resistance detection assay is a biological test as it directly measures the biological effect a drug has on tuberculosis. While previous biological tests were growth based and took several weeks to identify a difference in bacterial growth between drug treated and untreated samples, FASTPLAQUE-RESPONSE™ is a rapid biological test that does not measure cell growth. Instead, it uses the mycobacteriophage D29 to measure an antimicrobial's effect on host cell metabolism. Although an accurate and rapid test, FASTPLAQUE-RESPONSE™ is too complicated and unwieldy for use in resource-poor settings because the analysis of viral growth by plaque formation on agar plates must be performed in a laboratory by a trained technician.

Another phage-based system for the detection of Mtb drug resistance measures the enzymatic activity of a single phage-encoded polypeptide rather than the ability of the entire mycobacteriophage to replicate and spread as is done by FASTPLAQUE-RESPONSE™. This system was originally developed by researchers at Albert Einstein College of Medicine and is known as the Luciferase Reporter Assay (LRA). The LRA utilizes a recombinant version of the mycobacteriophage TM4 that has been engineered to highly express the luciferase gene from the firefly *Photinius pyralis*. Luciferase is a single subunit enzyme that, upon cleavage of its substrate luciferin in the presence of ATP and molecular oxygen, releases a photon of light. The presence of luciferase can thus be measured by detecting its light production. During Luciferase Reporter Phage (LRP) infection of untreated Mtb, the luciferase polypeptide accumulates and its enzymatic activity can be detected by measuring photon production after adding luciferin, which readily enters Mtb cells. Incubation of drug susceptible Mtb with appropriate anti-tuberculosis antibiotics either kills the cell outrightly or leads to a decrease in the metabolic capacity of the cell. Because Adenosine Triphosphate (ATP) is the essential source of potential energy in the cell and luciferase activity requires ATP for not only enzyme activity but also for the luciferase enzyme's synthesis, luciferase is an excellent indicator of a cell's metabolic capacity and hence the effect a given anti-microbial has on cell viability. During LRP infection of drug susceptible Mtb treated with an anti-tuberculosis antibiotic, luciferase enzyme synthesis and subsequent light production is dramatically reduced compared to an LRP infected control to which no anti-tuberculosis antibiotic was added. This differential in luciferase activity demonstrates an anti-microbial's effectiveness against Mtb. However, if light production in drug-treated and LRP infected Mtb is similar to an untreated control, the Mtb isolate is identified as drug resistant. The LRA has been evaluated in clinical trials testing Mtb resistance to first line anti-microbials and shown to have greater than 90% sensitivity and 100% specificity. Although an excellent tool to speed detection of drug resistant Mtb, only very sophisticated luminometers can detect luciferase light production from the small numbers of bacteria present in a clinical specimen. The LRA is thus not amenable to use in resource-poor settings that do not have the capacity to purchase and operate a luminometer.

Recent efforts to rapidly identify drug resistance directly from clinical specimens employ nucleic acid amplification (NAA) to detect specific Mtb genomic loci that confer resistance to commonly used anti-tuberculosis drugs. One example is Hain Lifescience's (Nehren, Germany) GENOTYPE® MtbDR, which uses a pregnancy test-like lateral flow strip to detect specific drug resistance alleles amplified from clinical sample-derived Mtb DNA. GENOTYPE® MtbDR is proving very complicated and expensive as there are over 15 commonly observed known mutations that confer resistance to RIF and INH. Another molecular diagnostic technology in development by Cepheid (Sunnyvale, Calif.) is intended only for diagnosis of RIF resistance in Mtb. Cepheid's market advantage is mostly due to the GENEXPERT® system, which fully automates sample processing and NAA. However, detection of the individual resistance loci in the amplification reaction requires fluorescent probes that are expensive to synthesize and require sophisticated detection hardware. Because of this limitation, the Cepheid product is limited to detecting the five major mutations involved in Rifampicin resistance. For Cepheid to simultaneously detect both RIF and INH resistance loci would be too unwieldy and expensive.

All currently available molecular diagnostic technologies fail to satisfy today's need for effective diagnostics as they are incapable of detecting Mtb strains that are RIF or INH resistant but harbor uncharacterized mutations. They also fail to identify isolates resistant to other first-line antibiotics, much less XDR-TB strains, because the full gamut of clinically relevant mutations conferring resistance to all anti-Tb drugs is not known. A rapid molecular diagnostic test able to identify all drug-resistant Mtb strains, including emergent XDR-TB, will be an important and necessary tool for the effective treatment and control of drug-resistant tuberculosis. The development of such rapid molecular testing technology would also be relevant and important for other diseases including, but not limited to, cholera, cryptosporidiosis, leishmaniasis, meningitis, and pneumonia. Additionally, the development of accurate molecular testing enabling the detection of microbes would also be useful for the detection of contaminants in pollutants ranging in sample type from drinking water to laboratory reagents.

Mycobacterial Disease

Mycobacterial infections often manifest as diseases such as tuberculosis. Human infections caused by mycobacteria have been widespread since ancient times, and tuberculosis remains a leading cause of death today. Although the incidence of the disease declined, in parallel with advancing standards of living, since the mid-nineteenth century, mycobacterial diseases still constitute a leading cause of morbidity and mortality in countries with limited medical resources. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent. Nearly one third of the world's population is infected with *Mycobacterium tuberculosis* complex, commonly referred to as tuberculosis, with approximately 8 million new cases, and two to three million deaths attributable to tuberculosis yearly. Tuberculosis is the cause of the largest number of human deaths attributable to a single etiologic agent (see Dye et al., J. Am. Med. Association, 282, 677-686, (1999); and 2000 WHO/OMS Press Release).

After decades of decline, tuberculosis is now on the rise. In the United States, up to 10 million individuals are believed to be infected. Almost 28,000 new cases were reported in 1990, constituting a 9.4 percent increase over 1989. A sixteen percent increase in tuberculosis cases was observed from 1985 to 1990. Overcrowded living conditions and shared air spaces are especially conducive to the spread of tuberculosis, contributing to the increase in instances that have been observed among prison inmates, and among the homeless in larger U.S. cities. Approximately half of all patients with "Acquired Immune Deficiency Syndrome" (AIDS) will acquire a mycobacterial infection, with tuberculosis being an especially devastating complication. AIDS patients are at higher risks of developing clinical tuberculosis, and anti-tuberculosis treatment seems to be less effective than in non-AIDS patients. Consequently, the infection often progresses to a fatal disseminated disease.

*Mycobacteria* other than *M. tuberculosis* are increasingly found in opportunistic infections that plague the AIDS patient. Organisms from the *M. avium-intracellulare* complex (MAC), especially serotypes four and eight, account for 68% of the mycobacterial isolates from AIDS patients. Enormous numbers of MAC are found (up to 1010 acid-fast bacilli per gram of tissue), and consequently, the prognosis for the infected AIDS patient is poor.

The World Health Organization (WHO) continues to encourage the battle against tuberculosis, recommending prevention initiatives such as the "Expanded Program on Immunization" (EPI), and therapeutic compliance initiatives such as "Directly Observed Treatment Short-Course" (DOTS). For the eradication of tuberculosis, diagnosis, treatment, and prevention are equally important. Rapid detection of active tuberculosis patients will lead to early treatment by which about 90% cure is expected. Therefore, early diagnosis is critical for the battle against tuberculosis. In addition, therapeutic compliance will ensure not only elimination of infection, but also reduction in the emergence of drug-resistance strains.

The emergence of drug-resistant *M. tuberculosis* is an extremely disturbing phenomenon. The rate of new tuberculosis cases proven resistant to at least one standard drug increased from 10 percent in the early 1980's to 23 percent in 1991. Compliance with therapeutic regimens, therefore, is also a crucial component in efforts to eliminate tuberculosis and prevent the emergence of drug resistant strains. Equally important is the development of new therapeutic agents that are effective as vaccines, and as treatments, for disease caused by drug resistant strains of mycobacteria.

Multidrug-resistant tuberculosis (MDR-TB) is a form of tuberculosis that is resistant to two or more of the primary drugs used for the treatment of tuberculosis. Resistance to one or several forms of treatment occurs when bacteria develop the ability to withstand antibiotic attack and relay that ability to their progeny. Since an entire strain of bacteria inherit this capacity to resist the effects of various treatments, resistance can spread from one person to another.

The World Health Organization (WHO) estimates that up to 50 million persons worldwide may be infected with drug resistant strains of tuberculosis. Also, 300,000 new cases of MDR-TB are diagnosed around the world each year and 79 percent of the MDR-TB cases now show resistance to three or more drugs routinely used to treat tuberculosis. According to WHO, nearly 1 billion people will be infected with tuberculosis within the next decade if more effective preventative procedures are not adopted.

In 2003, the CDC reported that 7.7 percent of tuberculosis cases in the U.S. were resistant to isoniazid, a first line drug used to treat tuberculosis. The CDC also reported that 1.3 percent of tuberculosis cases in the U.S. were resistant to both isoniazid and rifampicin. Rifampicin is the drug most commonly used with isoniazid.

Clearly, the possibility of drug resistant strains of tuberculosis that develop during or before treatment are a major concern to health organizations and heath care practitioners. Drugs used in the treatment of tuberculosis include, but are not limited to, ethambutol, pyrazinamide, streptomycin, isoniazid, moxifloxacin and rifampicin. The exact course and duration of treatment can be tailored to a specific individual, however several strategies are well known to those skilled in the art.

Although over 37 species of mycobacteria have been identified, more than 95% of all human infections are caused by six species of mycobacteria: *M. tuberculosis, M. avium intracellulare, M. kansasii, M. fortuitum, M. chelonae*, and *M. leprae*. The most prevalent mycobacterial disease in humans is tuberculosis, which is predominantly caused by mycobacterial species comprising *M. tuberculosis, M. bovis*, or *M. africanum* (Merck Manual 1992). Infection is typically initiated by the inhalation of infectious particles which are able to reach the terminal pathways in lungs. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately eliminated. The disease is further disseminated during the initial stages by the infected macrophages which travel to local lymph nodes, as well as into the blood stream and other tissues such as the bone marrow, spleen, kidneys, bone and central nervous system. (See Murray et al. *Medical Microbiology*, The C.V. Mosby Company 219-230 (1990)).

There is still no clear understanding of the factors that contribute to the virulence of mycobacteria. Many investigators have implicated lipids of the cell wall and bacterial surface as contributors to colony morphology and virulence. Evidence suggests that C-mycosides, on the surface of certain mycobacterial cells, are important in facilitating survival of the organism within macrophages. Trehalose 6,6' dimycolate, a cord factor, has been implicated for other mycobacteria.

The interrelationship of colony morphology and virulence is particularly pronounced in *M. avium. M. avium* bacilli occur in several distinct colony forms. Bacilli which grow as transparent, or rough, colonies on conventional laboratory media are multiplicable within macrophages in tissue culture, are virulent when injected into susceptible mice, and are resistant to antibiotics. Rough or transparent bacilli, which are maintained on laboratory culture media, often spontaneously assume an opaque R colony morphology, at which time they are not multiplicable in macrophages, are avirulent in mice, and are highly susceptible to antibiotics. The differences in colony morphology between the transparent, rough and opaque strains of *M. avium* are almost certainly due to the presence of a glycolipid coating on the surface of transparent and rough organisms which acts as a protective capsule. This capsule, or coating, is composed primarily of C-mycosides which apparently shield the virulent *M. avium* organisms from lysosomal enzymes and antibiotics. By contrast, the non-virulent opaque forms of *M. avium* have very little C-mycoside on their surface. Both the resistance to antibiotics and the resistance to killing by macrophages have been attributed to the glycolipid barrier on the surface of *M. avium*.

Traditional diagnosis of mycobacterial infection is confirmed by the isolation and identification of the pathogen, although conventional diagnosis is based on sputum smears, chest X-ray examination (CXR), and clinical symptoms. Isolation of mycobacteria on a medium takes as long as four to eight weeks. Species identification takes a further two weeks. There are several other techniques for detecting mycobacteria such as the polymerase chain reaction (PCR), *mycobacterium tuberculosis* direct test, or amplified *mycobacterium tuberculosis* direct test (MTD), and detection assays that utilize radioactive labels. Most of these tests are often cumbersome, require high level of technical expertise and require long periods of time before useful results can be obtained.

One diagnostic test that is widely used for detecting infections caused by *M. tuberculosis* is the tuberculin skin test. Although numerous versions of the skin test are available, typically one of two preparations of tuberculin antigens are used: old tuberculin (OT), or purified protein derivative (PPD). The antigen preparation is either injected into the skin intradermally, or is topically applied and is then invasively transported into the skin with the use of a multiprong inoculator (Tine test). Several problems exist with the skin test diagnosis method. For example, the Tine test is not generally recommended because the amount of antigen injected into the intradermal layer cannot be accurately controlled (see Murray et al., *Medical Microbiology*, The C.V. Mosby Company 219-230 (1990)).

Although the tuberculin skin tests are widely used, they typically require two to three days to generate results, and many times, the results are inaccurate since false positives are sometimes seen in subjects who have been exposed to mycobacteria, but are healthy. In addition, instances of mis-diagnosis are frequent since a positive result is observed not only in active tuberculosis patients, but also in persons vaccinated with Bacille Calmette-Guerin (BCG), and those who had been infected with mycobacteria, but have not developed the disease. It is hard, therefore, to distinguish active tuberculosis patients from the others, such as household tuberculosis contacts, by the tuberculin skin test. Additionally, the tuberculin test often produces a cross-reaction in those individuals who were infected with mycobacteria other than *M. tuberculosis* (MOTT). Therefore, diagnosis using the skin tests currently available is frequently subject to error and inaccuracies.

The standard treatment for tuberculosis caused by drug-sensitive organisms is a six-month regimen consisting of four drugs given for two months, followed by two drugs given for four months. The two most important drugs, given throughout the six-month course of therapy, are isoniazid and rifampicin. Although the regimen is relatively simple, its administration is quite complicated. Daily ingestion of eight or nine pills is often required during the first phase of therapy; a daunting and confusing prospect. Even severely ill patients are often symptom free within a few weeks, and nearly all appear to be cured within a few months. If the treatment is not continued to completion, however, the patient may experience a relapse, and the relapse rate for patients who do not continue treatment to completion is high. A variety of forms of patient-centered care are used to promote adherence with therapy. The most effective way of ensuring that patients are taking their medication is to use directly observed therapy, which involves having a member of the health care team observe the patient take each dose of each drug. Directly observed therapy can be provided in the clinic, the patient's residence, or any mutually agreed upon site. Nearly all patients who have tuberculosis caused by drug-sensitive organisms, and who complete therapy will be cured, and the risk of relapse is very low ("Ending Neglect: The Elimination of Tuberculosis in the United States" ed. L. Geiter Committee on the Elimination of Tuberculosis in the United States Division of Health Promotion and Disease Prevention, Institute of Medicine. Unpublished.)

The FDA approved a medication that combines the three main drugs (isoniazid, rifampicin, and pyrazinamide) used to treat tuberculosis into one pill. This reduces the number of pills a patient has to take each day and makes it impossible for the patient to take only one of the three medications, a common path to the development of MDR-TB. Despite this, there is still a need in the art to treat tuberculosis, especially in those cases wherein the tuberculosis strain is drug resistant.

What is needed are effective diagnostic and therapeutic tools to address the ever persisting and ever evolving challenges posed by infectious disease, in particular mycobacterial disease. In addition, as the use of antibiotics becomes increasingly widespread, and in some cases where the use of antibiotics is not in compliance with prescribed and recommended regimens, we find ourselves challenged with novel strains of infectious agents and microbes that no longer respond to standard therapies. What is needed therefore, are effective tools for identifying infectious agents, wherein such tools are also preferably capable of determining drug susceptibility. Importantly, what is needed are diagnostic tools that are easy to use, that require minimal testing time, and that are inexpensive so that they are readily available for use in parts of the world where the disease is rampant, and where resources are limited.

What is also needed are efficient, simple and accurate molecular testing technologies that enable the detection of infectious agents, that provide information concerning the viability of the infectious agent and that determine drug susceptibility. Use of such technologies would not be limited to infectious disease alone however, their utility could be extended to detection and evaluation of microbes and pollutants in a variety of samples ranging from biological to industrial.

SUMMARY OF THE INVENTION

The present invention comprises methods and compositions comprising novel biological systems for the detection of infectious agents and microbes, for molecular antibiotic resistance/susceptibility testing as well as assessing microbial viability. In particular, the present invention provides a system employing the techniques of phage-based biological detection of drug resistance with the speed and sensitivity of nucleic acid amplification (NAA)-based microbial identification. A novel feature of the invention described herein is that the technology extends the NAA-based microbial identification to determining viability and physiology of microbial infection. The unique methodologies of the present invention provide effective diagnostic and therapeutic tools for detecting known and evolving microbes, for providing viability status of such microbes as well as assessing drug susceptibility. The methods described herein are easy to use, require minimal testing time, and are inexpensive.

Nucleic acid amplification-based microbial detection technologies are very sensitive and can accurately identify the presence of very small numbers of infectious agents and microbes, such as bacteria in a biological sample. However, since such technologies are solely dependent upon detection of nucleic acid, they cannot distinguish the metabolic activity of the cell or even its structural integrity as cell nucleic acid is still present and detectable after cell death or lysis. Accordingly, at best the currently available technologies are effective at simply detecting the presence of specific nucleic acid without furnishing any useful information concerning the viability of the microbe or organism from which the nucleic acid originated. This is particularly complicated in situations where the sample being tested may itself be contaminated thereby resulting in false identification. In addition, because currently available technologies only detect nucleic acid without assessing the viability of the organism from where the nucleic acid originated, such tests are often positive even after successful antibiotic treatment because the dead bacterial DNA still reads as a positive. The methods described herein overcome the problems of the currently available devices as the presently described technology requires the incorporation of a surrogate marker locus (SML) into a viable cell, the SML is then amplified and detected by NAA-based technologies. Antibiotics that interfere with cell viability inhibit the generation of the SML and no amplification product is detected, thereby demonstrating that the antibiotic is effective against the infecting organism.

Another shortcoming of currently available technology is that most tests that assess antibiotic (or drug) susceptibility rely upon the detection of specific, pre-identified genetic mutations. As is well accepted by those skilled in the art, such reliance is highly problematic. There are often many separate, distinct mutations in a microbial genome that can encode resistance to an antibiotic or drug, nucleic acid-based methods of detecting resistance mutations are complex and rely on previous identification, characterization, and validation of clinically relevant resistance-conferring mutations. Tests designed upon such features can only be useful as long as resistance can accurately be restricted to known mutations, when reduced to practice this is seldom a safe or complete hypothesis. The presently described methods provide a unique solution for overcoming this limitation: instead of detecting specific, known, and validated cell-encoded mutations that confer resistance to a particular antibiotic/drug, the present technology does not require prior knowledge of the specific resistance conferring mutations encoded in the cellular genome because it creates a single new nucleic acid species (the SML) inside the cell that serves as a phenotypic readout of cell viability or drug resistance and, therefore, both greatly simplifies and increases the sensitivity of nucleic acid-based methods for detection of viable and/or drug-resistant cells.

Previous work has demonstrated the feasibility of adding bacteriophage to a biological sample and subsequently measuring phage metabolism and/or reproduction in order to determine if the biological sample contains viable or drug resistant host bacteria. While many bacteria are easily cultureable and replicate quickly, many others are either uncultureable or replicate too slowly in order to be directly detected by growth-based assays. The use of phage to probe a biological sample in order to determine if viable or if drug resistant host cells are present, has been shown to greatly increase the speed at which slow growing bacteria are detected. Additionally, phage can also speed the detection of fast growing bacteria because lytic phage replication occurs within one or two cell doublings, while cell growth-based detection methods require many more population doublings.

The presently described methods enable a general antibiotic susceptibility test (AST) that has the accuracy of biological AST as well as the sensitivity and speed of NAA-based detection. Furthermore, since the present invention does not rely on prior identification of mutations associated with drug resistance, it is applicable to the diagnosis of all forms of drug resistance that can be evaluated by in vitro assay of a drug's efficacy against the phage's host bacteria.

With slight modifications to its three modules: drug exposure, viral infection, and automated NAA-based detection, the presently described invention can be easily adapted to detect drug resistance in any and all bacterial pathogens infected by a virus and other similar systems. The system has the potential for particular utility in the determination of the resistance profile of slow-growing bacteria, for which traditional methods require a long time to diagnose. Such bacteria include for example, but are not limited to, *Mycobacterium avium, Legionella pneumophilia, Heliobacter pylori, Streptococcus adjacent, Rickettsia prowazekii*, and *Acinetobacter baumannii*.

In one embodiment, the presently described invention comprises a general phage-based biological assay for the detection of viable and/or antibiotic resistant bacteria wherein successful phage infection generates a distinct change in the phage and/or host cell nucleic acid sequence, modification, and/or metabolism that can be detected by various nucleic acid amplification technologies. Until the discoveries described herein had been conceived by the present inventors, no other entity had utilized phage to deliver to host cells exogenous functions that specifically and predictably alter phage and/or host cell nucleic acid and therefore serve as nucleic acid-based surrogate markers of cell viability. The advantage of this technological innovation is that it uniquely combines phage-based biological determination of cell viability with the speed and sensitivity of nucleic acid based detection technologies in order to provide a rapid and sensitive test for the presence of viable or drug-resistant bacteria in a biological sample.

Accordingly, it is an object of the present invention to provide methods and compositions for the diagnosis of diseases caused by infectious agents, microorganisms or microbes.

It is a further object of the present invention to provide methods and compositions for the diagnosis and detection of infectious diseases.

Another object of the present invention is to provide methods and compositions for the detection, treatment and prevention of mycobacterial disease including, but not limited to, tuberculosis.

Yet another object of the present invention is to provide methods and compositions for the effective diagnosis and detection of infectious diseases using nucleic acid amplification technology.

Another object of the present invention is to provide methods and compositions for the effective diagnosis and detection of mycobacterial disease using nucleic acid amplification technology.

Still another object of the present invention is to provide methods and compositions for the effective diagnosis and detection of infectious diseases using phage-based biological detection of drug resistance.

Another object of the present invention is to provide methods and compositions for the effective diagnosis and detection of mycobacterial diseases using phage-based biological detection of drug resistance.

Another object of the present invention is to provide methods and compositions for the effective diagnosis and detection of infectious diseases using nucleic acid amplification technology and phage-based biological detection of drug resistance.

Another object of the present invention is to provide methods and compositions for the effective diagnosis and detection of mycobacterial diseases using nucleic acid amplification technology and phage-based biological detection of drug resistance.

Yet another object of the present invention is to provide methods and compositions for the effective diagnosis and detection of infectious diseases using nucleic acid amplification technology and phage-based biological detection of drug resistance wherein the infectious disease is caused by bacterial, mycological, parasitic, and viral agents.

Another object of the present invention is to provide methods and compositions for the effective diagnosis and detection of infectious diseases using nucleic acid amplification technology and phage-based biological detection of drug resistance wherein the infectious disease is caused by *staphylococcus*, streptococcaceae, neisseriaaceae, cocci, enterobacteriaceae, pseudomonadaceae, vibrionaceae, *campylobacter*, pasteurellaceae, *bordetella, francisella, brucella*, legionellaceae, bacteroidaceae, gram-negative bacilli, *clostridium, corynebacterium, propionibacterium*, gram-positive bacilli, anthrax, *actinomyces, nocardia, mycobacterium, Helicobacter pylori, Streptococcus pneumoniae, Candida albicans, treponema, borrelia, leptospira, mycoplasma, ureaplasma, rickettsia*, chlamydiae, systemic mycoses, opportunistic mycoses, protozoa, nematodes, trematodes, cestodes, adenoviruses, herpesviruses, poxviruses, papovaviruses, hepatitis viruses, orthomyxoviruses, paramyxoviruses, coronaviruses, picornaviruses, reoviruses, togaviruses, flaviviruses, bunyaviridae, rhabdoviruses, human immunodeficiency virus and retroviruses.

Yet another object of the present invention is to provide methods and compositions for the effective diagnosis and detection of infectious diseases using nucleic acid amplification technology and phage-based biological detection of drug resistance wherein the infectious disease comprises, leprosy, Crohn's Disease, acquired immunodeficiency syndrome, lyme disease, cat-scratch disease, Rocky Mountain Spotted Fever and influenza.

Yet another object of the present invention is to provide methods and compositions for the effective diagnosis and detection of mycobacterial diseases using nucleic acid amplification technology and phage-based biological detection of drug resistance wherein the mycobacterial diseases comprises tuberculosis.

Yet another object of the present invention is to provide methods and compositions for the effective diagnosis and detection of mycobacterial disease caused by mycobacterial species comprising *M. tuberculosis* complex, *M. avium intracellulare, M. kansarii, M. fortuitum, M. chelonoe, M. leprae, M. africanum, M. microti, M. bovis* BCG or *M. bovis*.

Still another object of the present invention is to provide methods and compositions for the effective diagnosis and detection of infectious disease caused by *Mycobacterium-fortuitum, Mycobacterium marinum, Helicobacter pylori, Streptococcus pneumoniae* and *Candida albicans*.

Another object of the present invention is to provide methods and compositions for the effective detection of infectious agents and determining the viability of such infectious agents.

Yet another object of the present invention is to provide methods and compositions for the effective detection of infectious agents and determining the drug susceptibility of such infectious agents.

Another object of the present invention is to provide methods and compositions for the effective detection of infectious agents and determining the drug susceptibility of such infectious agents wherein the drugs comprise isoniazid, rifampicin, ethambutol, pyrazinamide, streptomycin, clofazimine, rifabutin, fluoroquinolones such as ofloxacin and sparfloxacin, azithromycin, clarithromycin, dapsone, tetracycline, doxycycline, erythromycin, ciprofloxacin, doxycycline, erythromycin, ampicillin, amphotericin B, ketoconazole, fluconazole, pyrimethamine, sulfadiazine, clindamycin, azithromycin, clarithromycin, atovaquone, pentamidine, paromomycin, diclazaril, acyclovir, trifluorouridine and other and type 2 antiviral nucleoside analogs, foscornat, antisense oligonucleotides, and triplex-specific DNA sequences, foscarnet, ganciclovir, AZT, DDI, DDC, foscarnet, viral protease inhibitors, peptides, antisense oligonucleotides, triplex and other nucleic acid sequences or ribavirin.

A further object of the present invention is to provide methods and compositions for the effective detection of infectious agents and determining the drug susceptibility of such infectious agents wherein the drugs comprise antibiotics.

An additional object of the present invention is to provide methods and compositions for the effective detection of infectious agents and determining the drug susceptibility of such infectious agents wherein the infectious agents comprise mycobacteria and wherein the drugs comprise antitubercular agents including, but not limited to, rifampicin, isoniazid, pyrazinamide, moxifloxacin and ethambutol and analogues thereof.

An additional object of the present invention is to provide methods and compositions for the effective detection of infectious agents and determining the drug susceptibility of such infectious agents wherein the infectious agents comprise mycobacteria and wherein the drugs comprise antitubercular agents including, but not limited to, rifampicin, and rifampicin analogues such as rifapentine, rifalazil and rifabutin.

Yet another object of the present invention is to provide methods and compositions for the effective detection of infectious agents and determining the drug susceptibility of such infectious agents wherein the methods are easy to administer and results are obtained 1-20 days, in 1-10 days, 0.5 hours to 10 days, 0.5-24 hours, 2-8 hours, and preferably in 2-4 hours.

It is a further object of the present invention to provide methods and compositions for the effective detection of infectious agents and determining the drug susceptibility of such infectious agents wherein the methods are automated.

These and other objects, features and advantages of the present invention will become apparent after a review of the following detailed description of the disclosed embodiments and the appended claims.

BRIEF DESCRIPTION OF THE FIGURES

FIG. 2A presents Hain's GenoType-MTBDR Test (Prior Art): DNA is isolated from a clinical sample and various Mtb genomic loci involved in resistance to INH and RIF are amplified. The amplification products are then analyzed via hybridization using Hain's DNA-Strip technology. Resistance to INH (INH-R) at allele B is observed in this example through the absence of the wildtype isoniazid susceptibility allele B (H-WT-B) and detection of the corresponding mutant allele which confers resistance to INH (HrB). FIG. 2B provides a schematic depicting the present invention: Resistance to INH is determined by incubating Mtb derived from a clinical sample in the presence of clinically relevant concentrations of INH followed by SML-Phage infection. The presence of Mtb and the SML is determined by amplifying the SML as well as IS9110, a region unique to Mtb (for Mtb ID). As would be evident to one skilled in the art, any region unique for the microbe of interest will serve the purpose of identifying the presence of that microbe in the sample. The amplification products are then analyzed as for GenoType MtbDR except that only the IS9110 and SML need be detected rather than upwards of thirty individual loci. The presence of the SML and IS9110 identify drug resistance while the presence of IS9110, but not the SML, diagnoses drug susceptibility.

FIG. 3A provides a diagramatic representation of Hain's GENOTYPE® MtbDR test (Prior Art): a complicated test designed to detect the many genes associated with resistance to both INH and RIF, which defines MDR-TB. In order to detect MDR-TB, this test must analyze upwards of 30 loci and simultaneously detect the presence of two drug resistance conferring alleles, one for INH and one for RIF while also demonstrating the absence of the corresponding WT alleles. In contrast, FIG. 3B shows how the present invention is simply adjusted to detect INH or RIF resistance, only one change must be made in manufacturing: inclusion of RIF with INH. Because the readout is the same (IS9110 and SML) regardless of which anti-Tuberculosis drug is used, the present invention is easily adaptable to the testing of any drugs either alone or in combinations.

The TM4 mycobacteriophage encodes a 53 kb double stranded linear DNA genome. All of its ORFs are encoded on one strand and all phage transcription occurs in one direction. phAE142 encodes the luciferase gene which is transcriptionally controlled by the gp71-regulatable $P_{left}$ promoter (star). The direction of $P_{left}$ transcription of the luciferase ORF in phAE142 is indicated by the dashed arrow. To create the RRP, the luciferase ORF is replaced with the Cre ORF and two loxP sites separated by an intervening DNA sequence. The loxP sites are oriented in opposition to one another to mediate inversion of the intervening DNA sequence. P1, P2, P3, and P4 indicate NAA primers that hybridize to unique DNA sequences (T1-T4) in the RRP and are used in the analysis of recombination products. In the unrecombined RRP, primer pairs P1-P3 and P2-P4 are capable of generating an NAA product.

Figure 5:
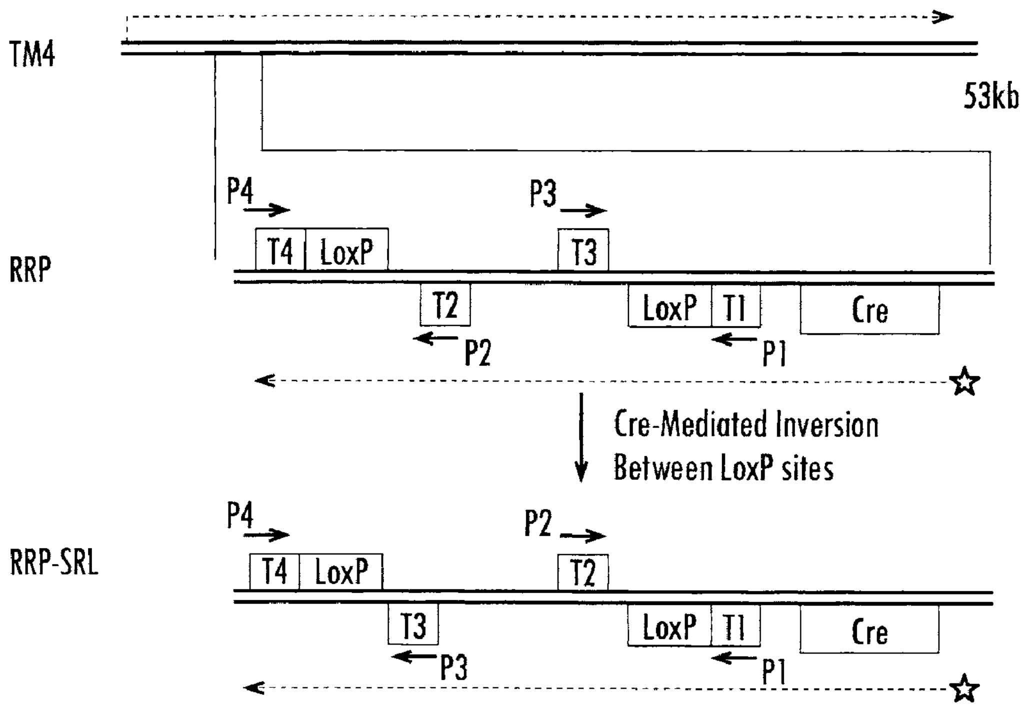

FIG. 5 provides a schematic showing SML generation in a RRP. During infection of a viable mycobacterial cell with the RRP, the Cre recombinase protein should be synthesized and mediate intramolecular recombination between the loxP sites of the virus. In this example, the orientation of the loxP sites are such that Cre will mediate inversion of the DNA sequence between the loxP sites. This inversion generates the SML because the area between, for example, primers P1 and P2, is not present in the original, unrecombined virus and an NAA product can be generated with this primer pair after recombinase mediated inversion. Primer pair P3-P4 will also be able to detect a new DNA sequence, or SML, in the virus.

Figure 6:
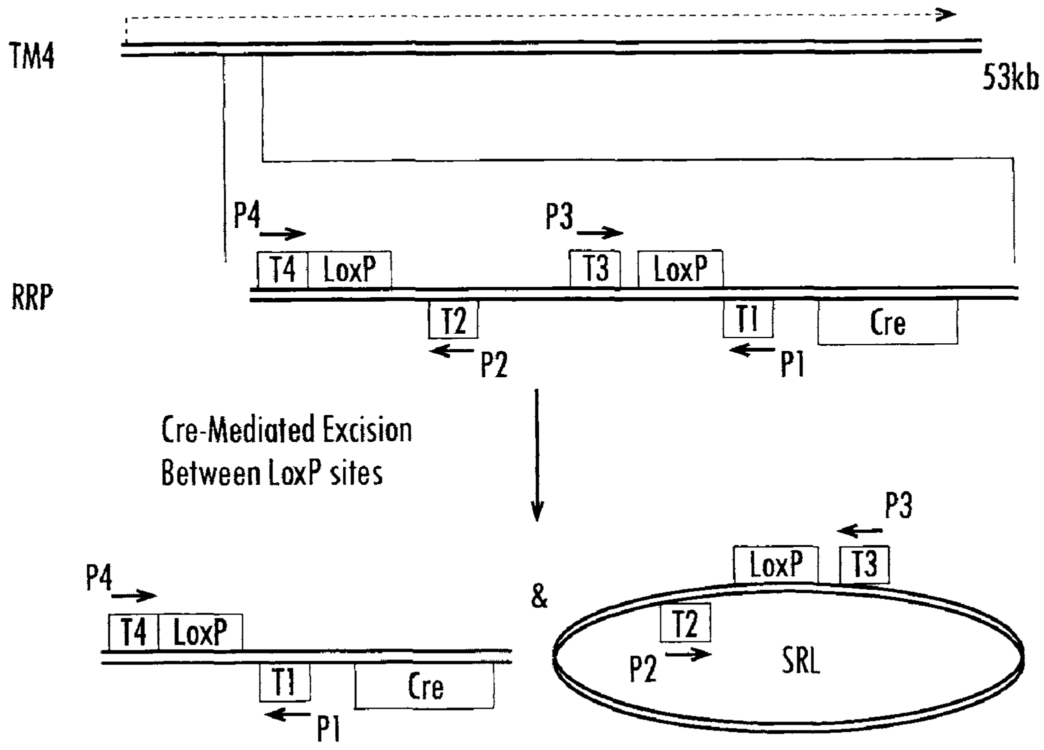

FIG. 6 provides a schematic showing Cre-mediated creation of SML via excision of intervening DNA sequence. When loxP sites are in identical orientations, i.e. not opposed, Cre mediated recombination excises the intervening sequence leaving one loxP site in the substrate and rendering the intervening sequence a circular DNA molecule with its own loxP site. In this construction, the SML is detected via NAA using primer pair P2-P3.

Figure 7:
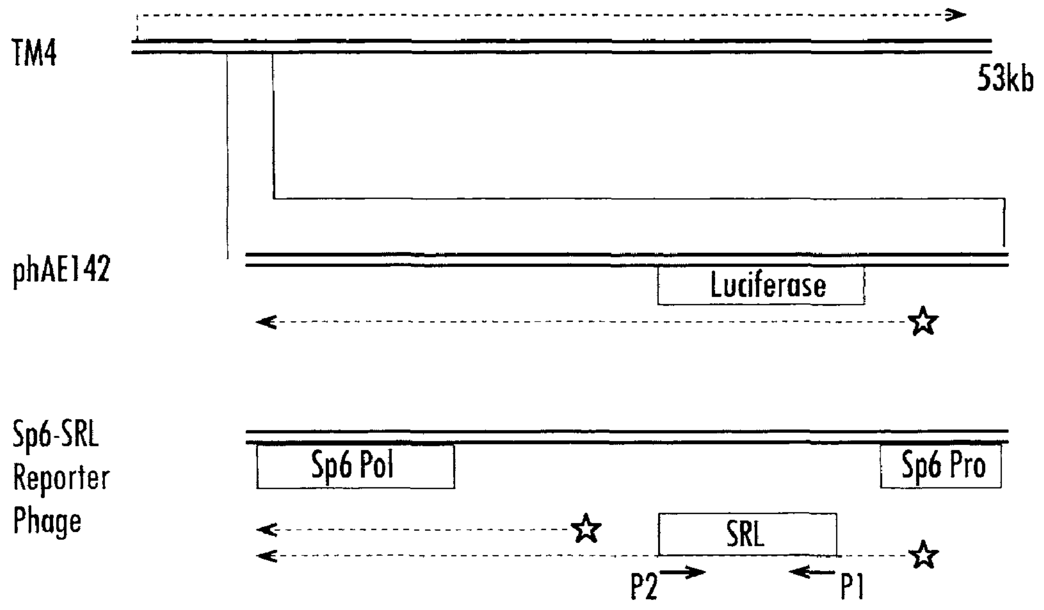

FIG. 7 provides the genetic structure of Sp6 RNA polymerase reporter phage. The direction of bona-fide phage transcription in TM4 based mycobacteriophages is depicted by the dashed arrow at the top of the figure. The genetic structure of the luciferase encoding locus in phAE412 is depicted and the direction of luciferase gene transcription from the $P_{left}$ promoter (grey star and associated arrow) is depicted. In generating the Sp6 RNA polymerase reporter phage, the luciferase gene of phAE142 is replaced with the SP6 RNA (and associated dashed arrow). Subsequently, the Sp6 promoter directing Sp6 RNA polymerase dependent transcription of a reporter sequence on the antisense strand relative to bonafide phage transcription is incorporated into a region that is thought to be transcriptionally silent on the antisense strand. Sp6-dependent transcription (red star and associated arrow) can be detected using primers P1 and P2 by NAA technologies that amplify RNA.

Figure 8:
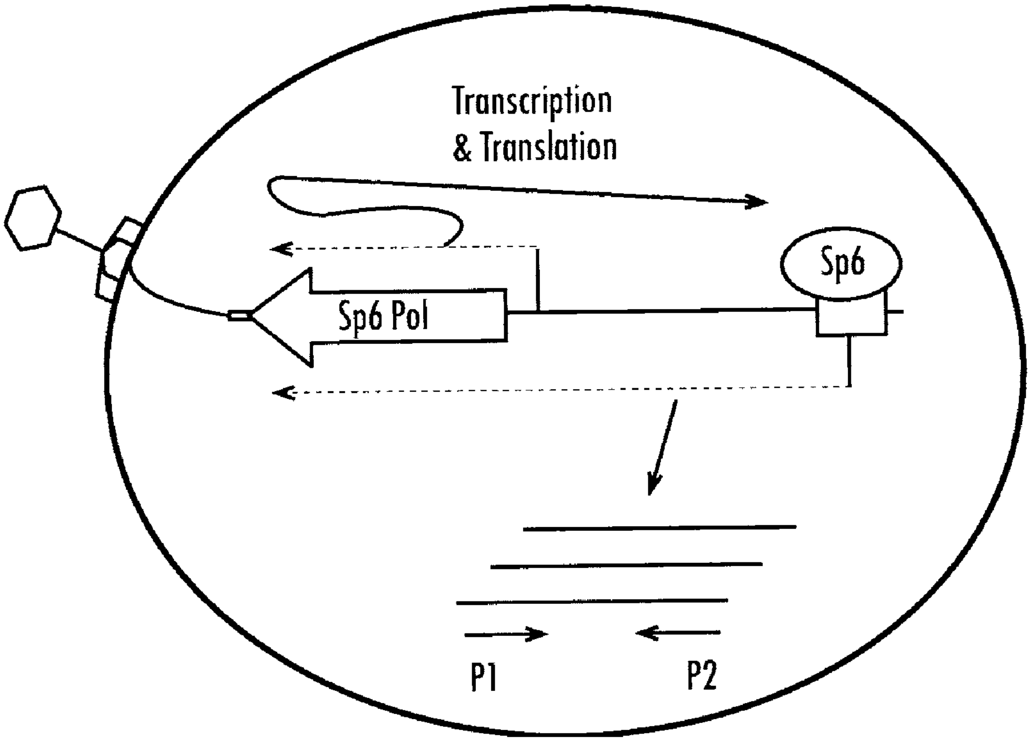

FIG. 8 provides a schematic depicting SML generation during infection with an Sp6 RNA polymerase reporter phage. Once the phage genome is inserted into the cell it is transcribed and translated on one strand. Once the Sp6 RNA polymerase is transcribed and translated, it directs transcription initiation from the Sp6 promoter sequence integrated into a transcriptionally silent locus. Because RNA can only be made from this locus, once Sp6 RNA polymerase is synthesized, it constitutes the SML and can be detected using appropriate primers in a RNA-based NAA reaction.

Figure 9:
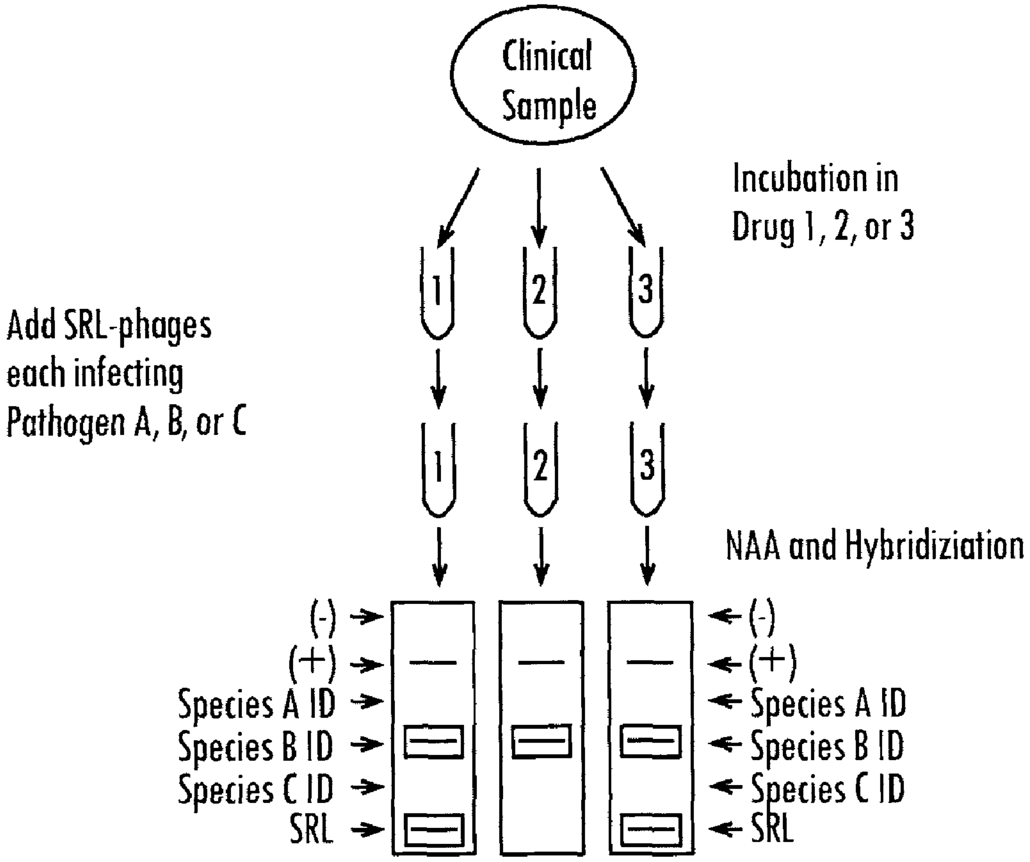

FIG. 9 provides a schematic showing a system for the simultaneous identification and AST of several geni or species of bacteria. A clinical sample is split between three (could be more or less) vessels, each containing a different antimicrobial (1, 2, or 3). After an appropriate incubation time, distinct species or geni-specific SML-phages which each infect either Pathogen A, B, or C are added and incubated an appropriate length of time to determine if Pathogen A, B, or C are present and resistant to any of the antimicrobials tested. Nucleic acid is then amplified and hybridized (or added) to a DNA-Strip-like assay system for analysis. In this example, Species B is the pathogen present in the clinical sample because its ID region is detected on all strips. The SML is detected after incubation with antimicrobials 1 and 3, but not 2. Drug 2 therefore kills Pathogen B, and should be prescribed to the patient.

Figure 10:
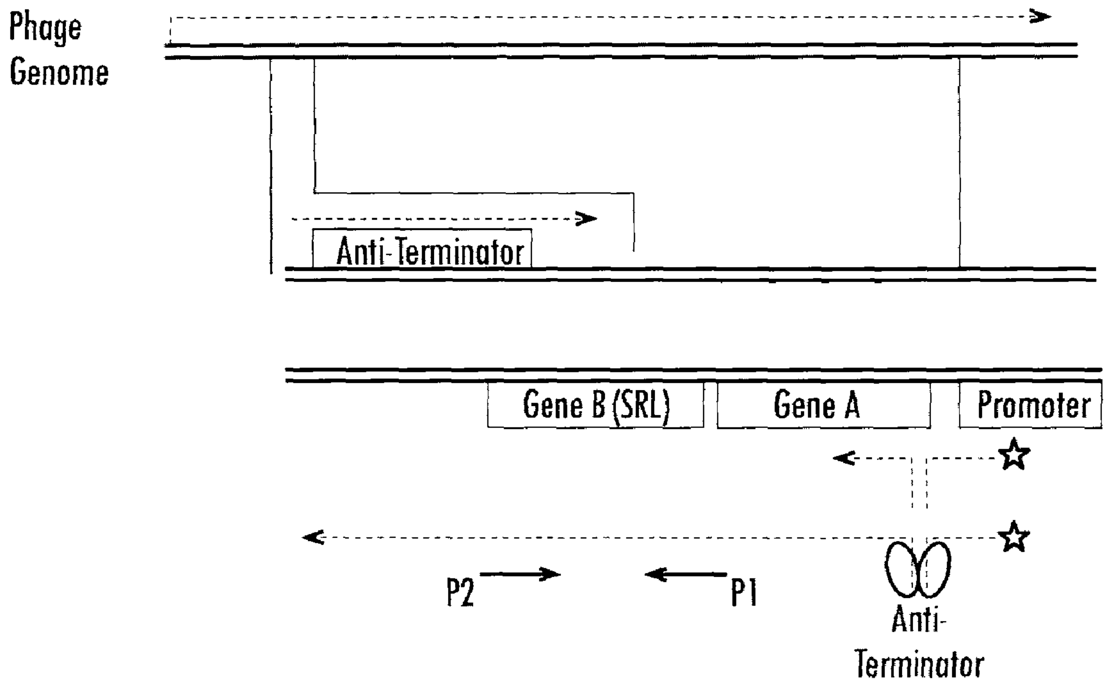

FIG. 10 provides a schematic showing a transcriptional regulatory mechanism in bacteriophage that can be used to detect "naturally occurring" SMLs (see Example 5).

Figure 11A:
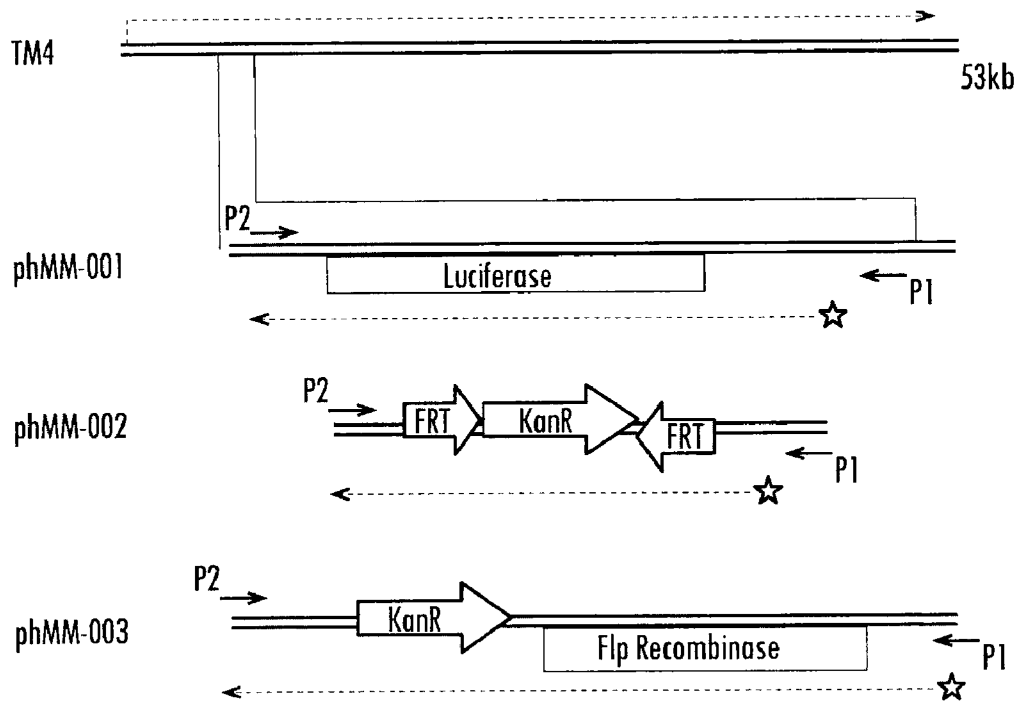
Figure 11B:
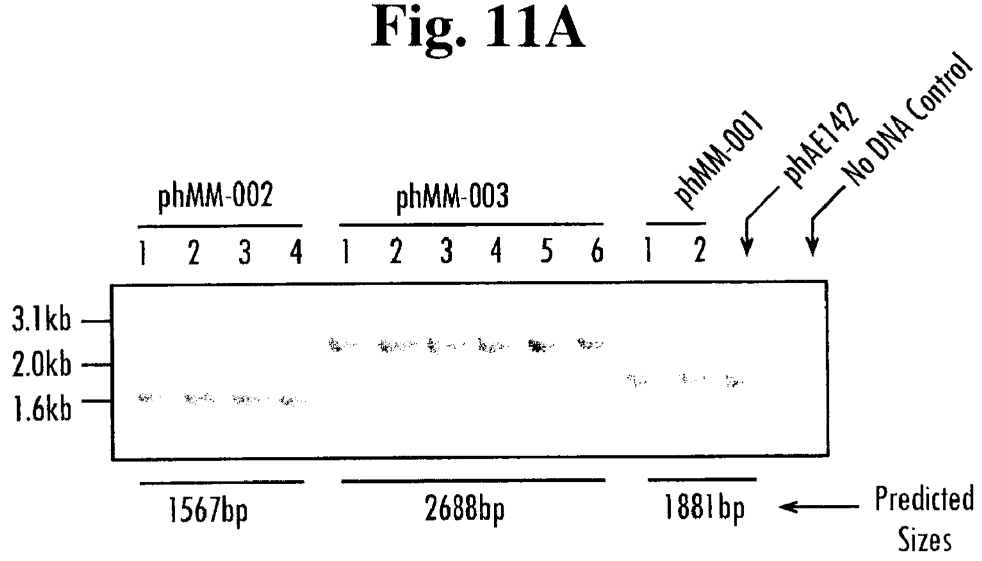

FIG. 11A provides a schematic diagram showing phMM-001, phMM-002, and phMM-003. FIG. 11B provides the results of an experiment conducted to verify the proper integration of the appropriate PCR products encoding the appropriate functions for phMM-002 and phMM-003 (see Example 6).

DETAILED DESCRIPTION

The present invention may be understood more readily by reference to the following detailed description of the specific embodiments included herein. However, although the present invention has been described with reference to specific details of certain embodiments thereof, it is not intended that such details should be regarded as limitations upon the scope of the invention. The entire text of the references mentioned herein are hereby incorporated in their entireties by reference including U.S. Provisional Patent Application Ser. No. 60/922,213, filed Apr. 5, 2007, U.S. Provisional Patent Application Ser. No. 60/927,287, filed May 1, 2007 and U.S. Provisional Patent Application Ser. No. 60/927,217, filed May 2, 2007.

Infectious agents, microbes and pathogenic organisms continue to be principal causes of illness and death in humans and animals. The development of molecular techniques to detect infectious agents and microbes has significantly contributed to early diagnosis of disease and development of therapeutics, both of which have diminished the severity of consequences resulting from infection in numerous cases. The detection of infectious agents, microbes, and foreign agents is important not only for managing direct pathogenic consequences of such organisms such as disease, but also for monitoring contamination in a myriad of scenarios ranging from pollutants in drinking water, to lingering microbes on lab equipment.

In addition to the detection of infectious agents, it has also become increasingly necessary to identify the viability status and the drug susceptibility of such infectious agents. Viability status is an important indicator of whether immunogenic therapy has been successful, and accurate drug susceptibility enables improved therapeutic intervention where drugs to which the organism is resistant are quickly ruled out and replaced with those predicted to have greater efficacy. As previously discussed, the medical community has seen an alarming rise in drug resistant infections and accordingly efficient, meaningful and early detection of pathogenic/infectious agents and microbes is a vital tool in providing patients with therapies that are likely to be successful.

An example of a disease causing particular concern is tuberculosis. Mycobacterial infections, such as those causing tuberculosis, once thought to be declining in occurrence, have rebounded, and again constitute a serious health threat.

Tuberculosis is the cause of the largest number of human deaths attributed to a single etiologic agent with two to three million people infected with tuberculosis dying each year. Areas where humans are crowded together, or living in sub-standard housing, are increasingly found to have persons affected with mycobacteria. Individuals who are immuno-compromised are at great risk of being infected with myco-bacteria and dying from such infection. In addition, the emergence of drug-resistant strains of mycobacteria has led to treatment problems of such infected persons.

Many people who are infected with mycobacteria are poor, or live in areas with inadequate healthcare facilities. As a result of various obstacles (economical, education levels, etc.), many of these individuals are unable to comply with the prescribed therapeutic regimens. Ultimately, persistent non-compliance by these and other individuals results in the prevalence of disease. This noncompliance is frequently compounded by the emergence of drug-resistant strains of myco-bacteria. Effective compositions and vaccines that target various strains of mycobacteria are necessary to bring the increasing number of tuberculosis cases under control. In addition, accurate detection and identification of drug susceptibility are equally important to improve a patient's survival and recovery.

Decades of misuse of existing antibiotics and poor compliance with prolonged and complex therapeutic regimens has led to mutations of *Mycobacterium tuberculosis* and has created an epidemic of drug resistance that threatens tuberculosis control worldwide. The vast majority of currently prescribed drugs, including the front line drugs, such as isoniazid, rifampicin, pyrazinamide, ethambutol and streptomycin were developed from the 1950s to the 1970s. Thus, this earlier development of tuberculosis chemotherapy did not have at its disposal the implications of the genome sequence of *Mycobacterium tuberculosis*, the revolution in pharmaceutical drug discovery of the last decades, and the use of national drug testing and combinational chemistry.

Consequently, the treatments of drug-resistant *M. tuberculosis* strains, and latent tuberculosis infections, require new anti-tuberculosis drugs that provide highly effective treatments, and shortened and simplified tuberculosis chemotherapies. In addition, in order to first effectively identify and treat patients with mycobacterial disease, it is necessary to have improved diagnostic protocols that not only result in the identification of the mycobacterial species, but also provide information with regard to drug susceptibility.

The present invention provides novel methods and compositions for the effective diagnosis and detection of infectious diseases using nucleic acid amplification technology and phage-based biological detection of drug resistance. The methods of the present invention are suitable for the detection of any infectious or contaminating agent and further provide relevant information regarding drug susceptibility. In addition, the methods of the present invention provide information concerning viability of the infectious or contaminating agent.

As used herein, the terms infectious agent, microbe, pathogenic organism, contaminating agent, comprise entities having the ability to cause infection, disease, contamination, illness and disruption of normal functioning in a host or environment being invaded.

The present invention comprises methods and compositions for the effective diagnosis and detection of infectious disease including, but not limited to, those caused by bacterial, mycological, parasitic, and viral agents. Examples of such infectious agents include the following: *staphylococcus*, streptococcaceae, neisseriaaceae, cocci, enterobacteriaceae, pseudomonadaceae, vibrionaceae, *campylobacter*, pasteurellaceae, *bordetella, francisella, brucella*, legionellaceae, bacteroidaceae, gram-negative bacilli, *clostridium, corynebacterium, propionibacterium*, gram-positive bacilli, anthrax, *actinomyces, nocardia, mycobacterium, Helicobacter pylori, Streptococcus pneumoniae, Candida albicans, treponema, borrelia, leptospira, mycoplasma, ureaplasma, rickettsia*, chlamydiae, systemic mycoses, opportunistic mycoses, protozoa, nematodes, trematodes, cestodes, adenoviruses, herpesviruses, poxviruses, papovaviruses, hepatitis viruses, orthomyxoviruses, paramyxoviruses, coronaviruses, picornaviruses, reoviruses, togaviruses, flaviviruses, bunyaviridae, rhabdoviruses, human immunodeficiency virus and retroviruses.

As used herein, the term "tuberculosis" comprises disease states usually associated with infections caused by mycobacteria species comprising *M. tuberculosis* complex. The term "tuberculosis" is also associated with mycobacterial infections caused by mycobacteria other than *M. tuberculosis* (MOTT). Other mycobacterial species include, but are not limited to, *M. avium-intracellulare, M. kansarii, M. fortuitum, M. chelonae, M. leprae, M. africanum, M. microti, M. avium paratuberculosis, M. intracellulare, M. scrofulaceum, M. xenopi, M. marinum*, and *M. ulcerans*.

The present invention further provides methods and compositions useful for the treatment of infectious disease including, but not limited to, tuberculosis, leprosy, Crohn's Disease, acquired immunodeficiency syndrome, lyme disease, cat-scratch disease, Rocky Mountain Spotted Fever and influenza.

As used herein, the phrase "pathogenic state" refers to the ability of an infectious agent, microbe or other biological agent to cause disease, illness or contamination and/or disrupt the normal metabolic, organic or physiologic function of a host organism or environment. The phrase may include reference to virulence, potential dormancy of the infectious agent, viability of the infectious agent and susceptibility to anti-infective intervention (for example, pharmaceutical/biochemical, drug (i.e. antibiotic) treatment).

As used herein, the phrase "metabolic state" refers to the processes that provide the ability of an organism to grow, reproduce, maintain structure and respond to its environment.

The novel methods of the present invention further enable the detection of drug susceptibility for various organisms. The table below (Table 1) provides a representative listing of pathogenic organisms and corresponding therapeutic agents. The methods of the present invention are applicable to, but not limited to, each of the examples provided in the Table.

TABLE 1

| | |
|---|---|
| BACTERIA | |
| *Mycobacterium tuberculosis* | Isoniazid, rifampicin, ethambutol, pyrazinamide, streptomycin, clofazimine, rifabutin, fluoroquinolones such as ofloxacin and sparfloxacin |
| *Mycobacterium avium* | Rifabutin, rifampicin, azithromycin, clarithromycin, fluoroquinolones |
| *Mycobacterium leprae* | Dapsone |
| *Chlamydia trachomatis* | Tetracycline, doxycyline, erythromycin, ciprofloxacin |
| *Chlamydia pneumoniae* | Doxycycline, erythromycin |
| *Listeria monocytogenes* | Ampicillin |
| FUNGI | |
| *Candida albicans* | Amphotericin B, ketoconazole, fluconazole |
| *Cryptococcus neoformans* | Amphotericin B, ketoconazole, fluconazole |

TABLE 1-continued

| | |
|---|---|
| PROTOZOA | |
| *Toxoplasma gondii* | Pyrimethamine, sulfadiazine, clindamycin, azithromycin, clarithromycin, atovaquone |
| *Pneumocystis carinii* | Pentamidine, atovaquone |
| *Cryptosporidium* sp. | Paromomycin, diclazaril |
| VIRUS | |
| Herpes simplex virus type 1 | Acyclovir, trifluorouridine and other and type 2 antiviral nucleoside analogs, foscornat, antisense oligonucleotides, and triplex-specific DNA sequences |
| Cytomegalovirus | Foscarnet, ganciclovir |
| HIV | AZT, DDI, DDC, foscarnat, viral protease inhibitors, peptides, antisense oligo-nucleotides, triplex and other nucleic acid sequences |
| Influenza virus types A & B | Ribavirin |
| Respiratory syncytial virus | Ribavirin |
| Varizella zoster virus | Acyclovir |

The methods of the present invention may be used to detect infectious agents, microbes and organisms of interest in a variety of samples including, but not limited to, body fluids (such as sputum, tears, saliva, sweat, mucus, serum, semen, urine and blood), research test samples, environmental samples (such as water samples, including water samples selected from natural bodies of water, ponds, community water reservoirs, recreational waters, swimming pools, whirlpools, hot tubs, spas, water parks, naturally occurring fresh waters, and marine surface waters) and industrial samples (such as fermenting inoculums (such as Lactobacteria), chemical reagents, culture media, cleaning solutions).

In summary, the novel methods of the present invention comprise the creation of a nucleic acid marker (NAM) through the creation of a Surrogate Marker Locus (SML). Phage encoded polypeptides mediate the creation of a NAM. Established NAA-technologies used for microbial detection specifically amplify and detect NAM to determine drug resistance. In one embodiment, such as an RNA based embodiment, the phage encodes a heterologous RNA polymerase. Infection of viable cells capable of protein synthesis leads to translation of the RNA polymerase. The polymerase then transcribes an otherwise absent RNA from its heterologous promoter inserted into the phage genome. NAM can be amplified using RNA-based NAA technologies and then detected.

The novel methods of the present invention uniquely combine the accuracy of phage-based biological detection of drug resistance with the speed and sensitivity of NAA-based microbial identification. This technology extends the NAA-based microbial identification to determining viability and physiology of the bacterial infection as well as determination of a complete susceptibility profile for any clinical isolate by observing the effect of antibiotics on microbial or bacterial physiology which, unlike prior art devices, includes any drugs of interest, irrespective of whether the genetic mutations responsible for the resistance are known. For example, because the genetic targets of only a few anti-tuberculosis drugs have been elucidated, and of those only a subset of mutations responsible for resistance have been identified, the present invention has significant advantages over all existing technologies. The same advantage is present for diseases other than tuberculosis also.

At least one unique aspect of the present invention is the use of a unique phage (SML-Phage) for the synthesis of a Surrogate Marker Locus (SML). Ideally, the same enzyme-SML reporter cassette would be inserted into existing phages that infect the bacteria (or target organism) of interest. At least one such enzyme-SML reporter cassette is described herein (see Examples and Figures). In certain cases, modifications (i.e. codon optimization) to the enzyme-reporter cassette may be necessary in order to make it function more efficiently in a specific host bacteria-phage system.

Although the introduction of nucleic acid into the bacteria or microbe is mainly described in terms of DNA introduction to bacteria via bacteriophages, as would be recognized by one skilled in the art, nucleic acid (including, but not limited to DNA and RNA) may also be introduced via other methods including, but not limited to, electric pulsing, electroporation, and osmotic shock.

In addition, in certain embodiments, more than one phage may be employed. In such embodiments, the phage may encode for more than one marker, enabling the monitoring of multiple characteristics of the organism or infectious agent.

After infection of Mtb exposed to any antimicrobial drug or combination of drugs (e.g. RIF and INH), an SML is synthesized by the unique phage (SML-Phage) of the present invention but only if the cell is still sufficiently metabolically active after drug treatment. Synthesis of the SML, therefore, provides information concerning the viability status of the Mtb organism. Accordingly, in the scenario where an individual has been infected with Mtb, but where the Mtb has responded to drug therapy (for example, has responded positively to RIF), an SML would not be generated. In contrast, however, use of traditional NAA-based microbial identification would be limited to the identification of Mtb, and no information would be available concerning drug susceptibility.

Figure 1:
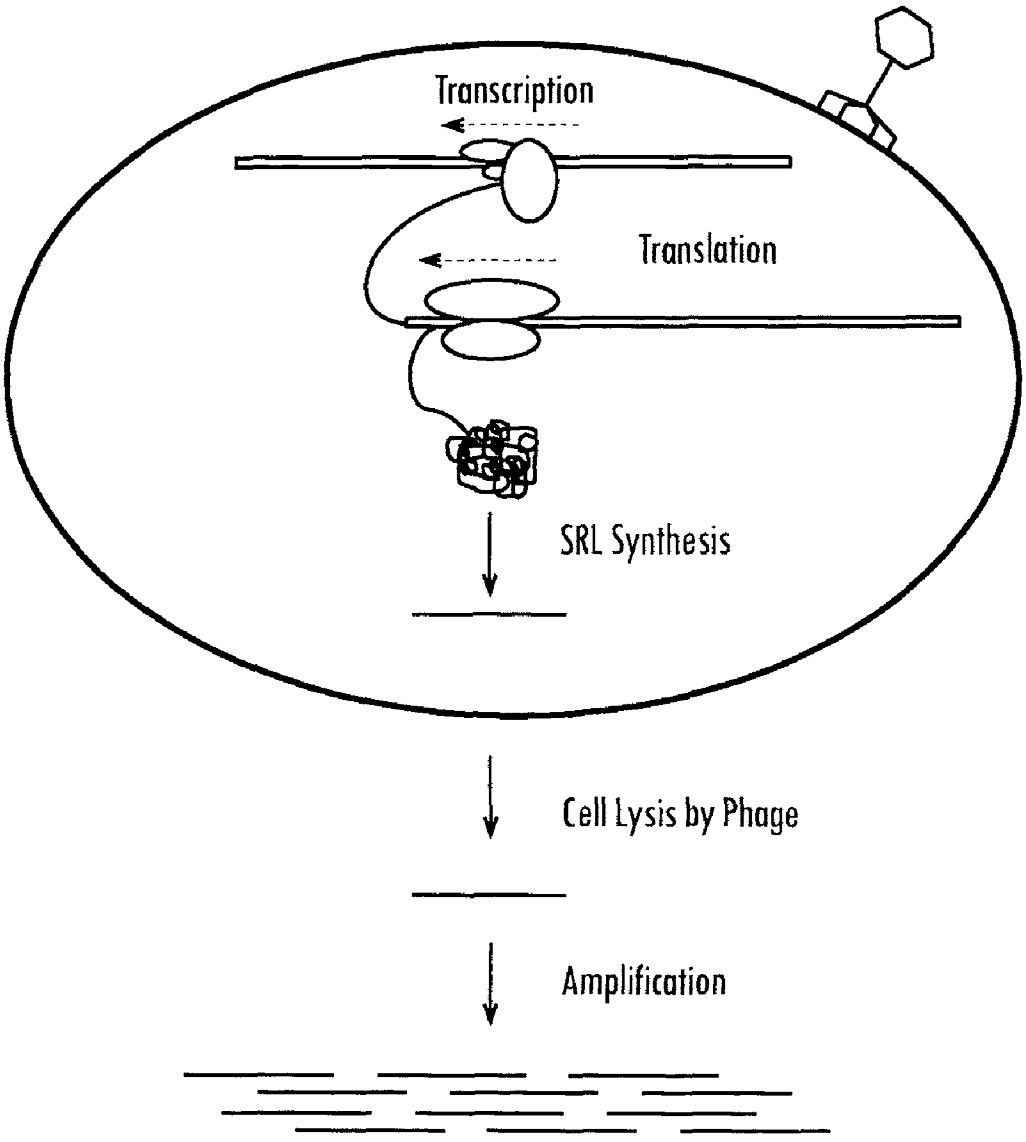
FIG. 1 provides a schematic showing the core technology of the present invention. The schematic demonstrates the infection of a viable Mtb by a mycobacteriophage encoding proprietary functions leading to the generation of a Surrogate Marker Locus (SML), which is then amplified and detected by established NAA-based technologies. Antibiotics that interfere with cell viability inhibit the generation of the SML and no amplification product is detected, demonstrating that the antibiotic is effective against Mtb. However, if Mtb is resistant to the drug, cellular metabolism is unaffected and the SML is synthesized, thereby demonstrating Mtb resistance to whichever drug was tested. Mtb is shown here as a representative infectious agent; as would be understood by one skilled in the art, Mtb may be replaced with a similar organism in the context of another disease or infectious state.
Figure 2A:
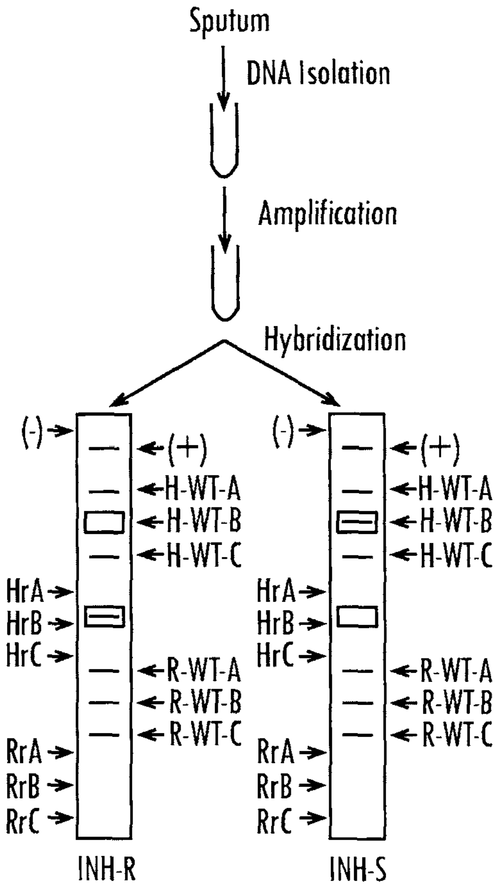
FIGS. 2A and 2B provide a comparative schematic showing how the presently described technology simplifies the molecular detection of drug resistance.
Figure 2B:
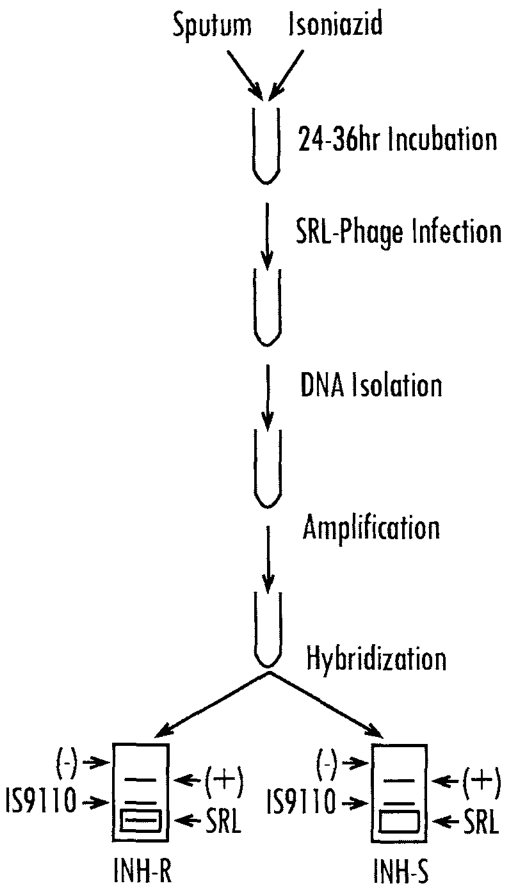
Figure 3A:
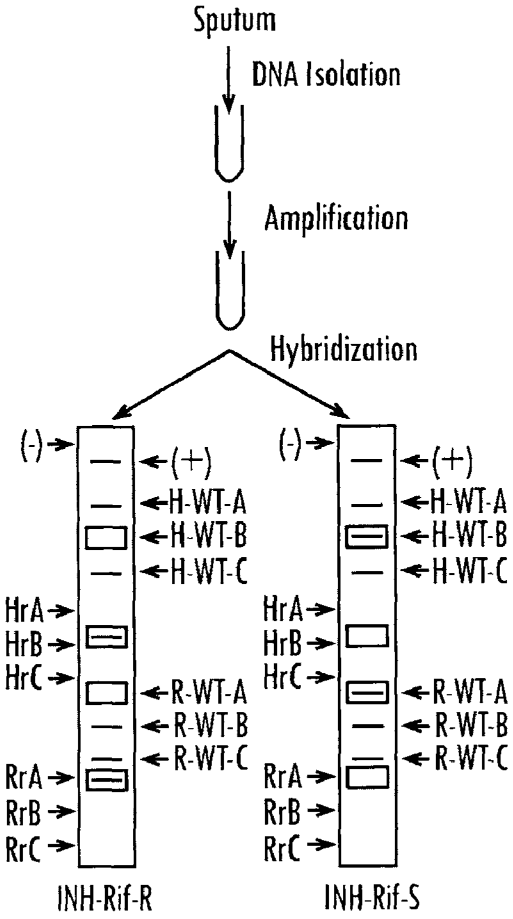
FIGS. 3A and 3B provide a comparative schematic demonstrating the adaptability of the present invention for the detection of MDR-TB.
Figure 3B:
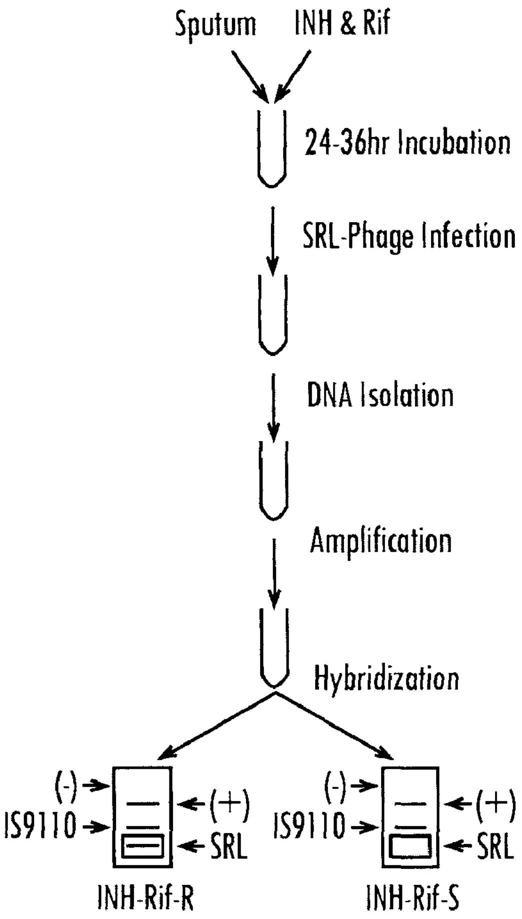

Another important feature of the present invention is the subsequent cell lysis by phage-encoded lysis functions, allowing the SML to be available for detection by established NAA-based molecular diagnostic technologies (FIG. 1). Lysis of Mtb by phage-encoded lysis functions precludes the need for mechanical cell lysis and simplifies the automation of the methods described herein. Hain's GENOTYPE® MtbDR test and Cepheid's GENEXPERT® require mechanical disruption of cell integrity in order to amplify and detect as many as 15 mutant and 15 wild-type alleles from Mtb (FIGS. 2A and 3A). In contrast, the methods of the present invention require no mechanical lysis, and must amplify and detect only two alleles: one for the identification of the organism (i.e. Mtb DNA) and the other for the phage-derived SML that is diagnostic of clinically relevant antibiotic resistance (FIGS. 2B and 3B).

One essential component of the invention described herein is the synthesis of the SML inside viable host cells. Synthesis of the SML comprises a unique bridge between the two general strategies for detecting drug resistance: biological testing and genetic testing.

Unlike detection devices currently available, the present invention is unique in that it is at once a biological and genetic test for cell viability or drug resistance because it requires the cell to be sufficiently intact and metabolically active to synthesize a phage-encoded function that mediates creation of the SML, the nucleic acid-based reporter of cell viability or drug resistance. Whereas the readouts of previous biological assays for drug resistance were either cellular growth, phage replication, or enzymatic light production, the present invention comprises technology wherein the biological readout is a new nucleic acid species, the SML, which can be detected using NAA-based detection technologies.

As compared to previous biological assays, the present invention provides greater utility because it relies in part upon NAA and detection. Molecular diagnostic companies have already developed simple, rapid and affordable devices for NAA and detection, and are continuing to make significant improvements thereon. In contrast, with regard to assays relying upon enzymatic light production, only very sophisticated luminometers can detect luciferase light production from the small numbers of bacteria present in a clinical specimen. Assays, such as luciferase light production assays, are not amenable to use in resource-poor settings that do not have the capacity to purchase and operate expensive luminometers.

Creation of the SML can be mediated by any of the following categories of polypeptide functions: DNA recombinases, RNA polymerases, polypeptides that direct RNA polymerase to transcribe a specific gene (transcription factors or sigma factors), DNA methylases, DNA demethylases, DNA restriction endonucleases, DNA ligases, RNA ligases, histone acetylases, histone deacetylases, uridine deaminases; and other such methods known to those skilled in the art with analagous functionality (i.e. requiring expression of a peptide which causes a change in a nucleic acid sequence either in the cell or provided by the bacteriophage which can be detected by a nucleic acid test).

The methods of the present invention simultaneously exploit the advantages of biological AST and simplify NAA-based detection of viability and drug resistance. In addition, the methods are more readily amenable to automation than currently available devices such as Biotec's FASTPLAQUE-RESPONSE™ because instead of measuring viral growth, already automated technologies can be used to detect the SML. Furthermore, the presently described methods utilizing SML technology greatly simplify the reagents and equipment needed to amplify and detect drug resistance-related loci, which makes the present invention excellent technology to be paired with existing molecular diagnostic systems.

An additional advantageous and important feature of the present invention is the time to detection (TTD) which ranges from approximately 1-20 days, or 1-10 days or 0.5 hours to 10 days; in an alternative embodiment, the TTD ranges approximately from 0.5-24 hours, 2-8 hours, and preferably in 2-4 hours.

This is on par with established rapid tests and clearly sufficient to enable timely implementation of appropriate antibiotic therapy (see Table 2: Comparison of Biotec's FASTPLAQUE-RESPONSE™, Hain Lifescience's GENOTYPE® MtbDR, Cepheid's GENEXPERT®, and methods of the present invention).

TABLE 2

| System | Type AST | Detection | Automated | TTD |
|---|---|---|---|---|
| FastPlaque-Response | Biological | Plaques on Agar plates | No | 3-4 days |
| GenoType MtbDR | Resistance Loci | DNA Strip | Automatable | 1 day |
| GeneXpert | Resistance Loci | Fluorescent Probes | Yes | 1 day |
| Present Invention | Biological and SML | DNA Strip or Fluorescent Probes | Easily Automatable | 2 hours |

Another desirable feature of the present invention is ability of the described methods to specifically detect viable organisms such as bacteria. Although the methods can be designed in such a way as to provide AST information, in certain embodiments where the drugs or antibiotics are omitted, the SML-phage technology can be used to provide sensitive and accurate detection of viable bacteria in a clinical sample. In such an embodiment wherein the AST feature is excluded (drugs or antibiotics are not included), molecular identification of pathogenic bacteria is no longer complicated by contamination of similar, but non-pathogenic, bacteria or the presence of dead bacteria. In contrast, current NAA-based microbial identification technologies cannot distinguish viable from dead bacteria. Because the SML is synthesized in viable bacteria, this method can be used for the accurate detection of viable bacteria in a clinical sample. Furthermore, in embodiments where antibiotic susceptibility is not necessary, the TTD is less than one day.

The following specific examples will illustrate the invention as it applies to the unique detection methods of the present invention. It will be appreciated that other examples, including minor variations in procedures, will be apparent to those skilled in the art, and that the invention is not limited to these specific illustrated examples.

Example 1

Novel Mycobacteriophage Recombinase System for Identifying Antimicrobial Resistant *Mycobacteria*

Figure 4:
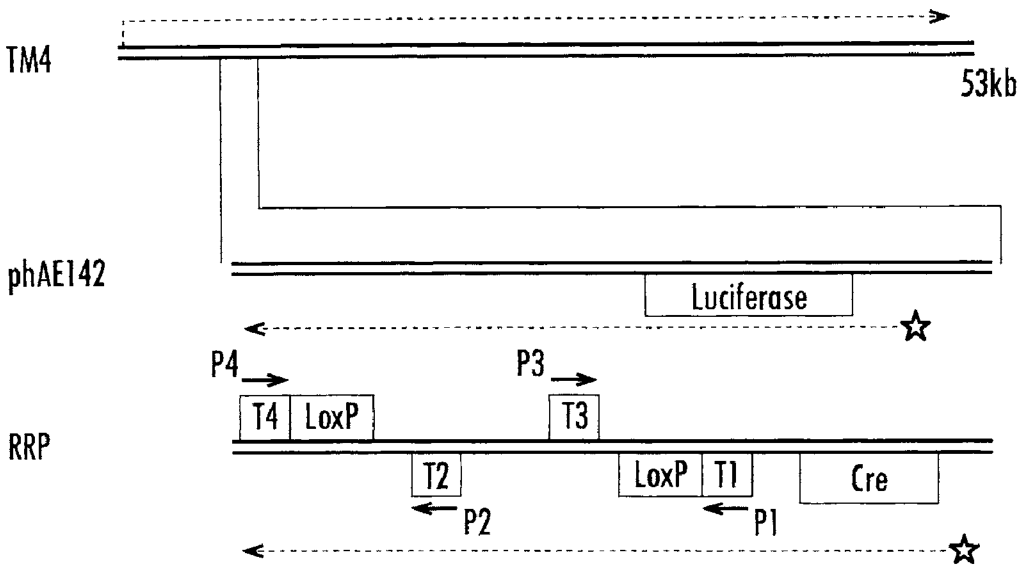
FIG. 4 provides the genetic structure of TM4, phAE142, and the Cre-encoding recombinase reporter phage (RRP).

Mycobacteriophages Encoding Transcriptionally Regulated Cre Recombinase and Signature Tagged LoxP Sites.

phAE142 is the mycobacteriophage currently used in the LRA assay (Albert Einstein College of Medicine, Bronx, N.Y.). High levels of luciferase enzyme are produced by placing its transcription under the control of the robust L5 $P_{left}$ promoter. An additional advantage of this promoter is that it is exquisitely silenced by the L5 gp71 polypeptide, thereby negating the toxic effects of luciferase to viral growth during preparation of high-titer stocks by using *Mycobacterium smegmatis* (M.smeg) host cells that constitutively express gp71. In the present invention, the luciferase open reading frame (ORF) of phAE142 is replaced with, for example, the Cre recombinase gene from bacteriophage P1 using established molecular biology techniques. Cre is under control of the $P_{left}$ promoter in order to prevent Cre-mediated generation of the SML during production of phage stocks. Two loxP sites are also placed downstream of the Cre ORF (FIG. 4). The Recombinase Reporter Phage (RRP) measures the metabolic activity of a mycobacterial cell during infection by directing the transcription and translation of the Cre recombinase which will subsequently bind the phage genome at the loxP sites and, because the loxP sites are oriented in opposition to one another, Cre will mediate inversion of the intervening DNA sequence. This inversion will change the DNA sequence of the phage genome, which constitutes generation of the SML. The SML can then be detected using primer pairs P1-P2 or P3-P4 using any NAA-based detection technology (FIG. 5).

Arrangement of the loxP sites so that they are oriented in the same direction will lead to Cre-mediated excision of the intervening sequence rather than inversion. In this instance, the SML would be generated in an excised circular DNA molecule (FIG. 6). This strategy may be more amenable to RRP manufacturing as any spurious generation of the SML during growth of phage stocks will not be contained in the infectious phage genome because the SML is part of a circular DNA molecule with no cos sites for packaging into the phage head. This spurious SML can be easily removed from the phage stock by size exclusion chromatography or similar separation methods.

Example 2

Novel Mycobacteriophage Transcription System for Identifying Antimicrobial-Resistant *Mycobacteria*

This example shows the rationale for an RNA-based SML reporter phage. This strategy employs the Sp6 RNA polymerase to generate an otherwise absent phage-encoded RNA. To accomplish this, the luciferase ORF of phAE142 is replaced with the Sp6 RNA polymerase from *Salmonella typhimirium* and is under $P_{left}$ transcriptional control. Additionally, the Sp6 promoter is integrated into an otherwise transcriptionally silent locus in the phage genome. Sp6-dependent RNA transcripts can then be detected using any NAA technology capable of detecting RNA.

RNA-Based SML Reporter Mycobacteriophage phAE142 is a TM4-based reporter phage. An advantageous feature of TM4 is that all of the known ORFs are contained on one strand of the double stranded genomic DNA and all are transcribed from a single promoter at one end of the genome (FIG. 7). Consequently, only one strand of phage RNA is transcribed during infection of *Mycobacteria*. Inclusion of the cognate DNA binding consensus sequence of a heterologous RNA polymerase into the phage genome in a transcriptionally silent locus renders that locus transcriptionally regulated by the heterologous RNA polymerase. Therefore, if the RNA polymerase is also integrated into the phage genome in a transcriptionally active locus, RNA transcription from the cognate promoter sequence should commence once the RNA polymerase is synthesized. In this formulation, RNA transcribed from the Sp6 promoter in an Sp6 RNA polymerase dependent fashion constitutes generation of the SML (see FIG. 8).

Examples 3-4

The following examples incorporate SML-phage technology of the present invention into Hain's GENOTYPE® MtbDR test, an existing genetic test for Mtb drug resistance, in order to demonstrate how present invention simplifies molecular-genetic tests for drug resistance and how it can be expanded to detect resistance to any drug. Furthermore, other applications of the present invention for the detection of viable and drug resistant bacteria are illustrated. Either of the two types of SML reporter phages explained in the previous examples can be used in the following examples depending on which method of NAA is used: DNA or RNA-based (e.g. PCR or RT-PCR).

Example 3

FIGS. 2A & 2B illustrate how SML-phage technology can be used to marry the accuracy of biological AST with the speed and sensitivity of NAA-based microbial detection methods. The Hain Lifescience GENOTYPE® MtbDR test amplifies DNA isolated from a clinical specimen, in this case sputum, using primer sets specific for certain Mtb genes involved in resistance to both Isoniazid (INH) and Rifampicin (RIF). Hain's core technology is the DNA-Strip: a pregnancy test-like lateral flow assay capable of discriminating single base substitutions in small pieces of DNA. After application of the amplification reaction products to the DNA-Strip, the products hybridize to completely homologous probe sequences immobilized on the DNA-Strip. This assay detects both the wildtype and mutant alleles of several mutations involved in resistance to RIF and INH. Although only three base substitution mutations involved in each form of drug resistance are shown in the figure, the actual Hain product is much more complicated as there are over 15 common individual point mutations involved in clinical resistance to both INH and RIF. FIG. 2A shows the general strategy for resistance mutation detection in the GenoType-MtbDR product. For Mtb to be identified as resistant to INH (INH-R) one of the mutant alleles conferring resistance to INH (HrB) must be detected while the corresponding WT allele (H-WT-B) must not be detected. If all WT alleles but none of the alleles involved in drug resistance are detected, then the isolate is identified as INH-susceptible (INH-S). The present invention can greatly simplify this system while expanding it to include detection of all clinical INH resistant strains by replacing all the WT and mutant alleles involved in drug resistance with the single SML. As shown in FIG. 2B, by incubating the sputum with INH for 24-36 hours and subsequently infecting Mtb with an SML-phage, detection of the SML after amplification diagnoses the presence of viable bacteria after incubation with INH. Because the phage was able to infect the cells and synthesize a phage-encoded polypeptide that mediates the creation of the SML, the cells are thus resistant to the effects of INH. As is clearly shown in FIG. 2, the advantage of the presently described SML-phage technology is that it is now possible for a biological assay of drug resistance to be analyzed through a simplified version of a current NAA-based molecular diagnostic technology.

While Hain's GENOTYPE® MtbDR test cannot cover all instances of INH and RIF drug resistance, even with upwards of thirty loci analyzed using DNA-Strip, the present invention can test for resistance to any relevant drug by simply changing the antibiotic used to incubate Mtb isolated from a clinical sample. FIGS. 3A and 3B demonstrates how the present invention technology can be used to detect multi-drug resistant Mtb, which is defined as resistance to both RIF and INH. While Genotype MtbDR requires that two resistance associated alleles, one for INH and one for RIF must be detected along with the absence of the corresponding WT alleles, simply adding both INH and RIF together during incubation of Mtb prior to phage infection accomplishes the better goal of phenotypically demonstrating RIF and INH resistance rather than inferring it from small mutations in the Mtb genome. The biological detection of drug resistance, because it measures phenotype, not genotype, is inherently more accurate and comprehensive than individually detecting the most common resistance mutations observed in the clinic. Furthermore, Hain's DNA-Strip technology must differentiate single base pair hybridization differences while SML-phage technology simply requires the detection of wholly different segments of nucleic acid, an approach that is significantly less prone to hybridization artifacts. Moreover, the present invention allows for the rapid generation of new AST devices for detecting emergent drug resistance for new antimicrobials or for ones that little is known about the molecular-genetic bases for clinically relevant drug resistance.

The readout of the present invention for multidrug resistance is the same as for single-drug resistance: SML synthesis. This allows the same NAA and detection system to be used for all products relating to Mtb drug resistance. This should dramatically lower the cost and difficulty in manufacturing individual tests for all permutations of Mtb drug resistance:

1. MDR-TB test (INH and RIF resistance)
2. Resistance to individual first line drugs (INH, RIF, Ethambutol, or Streptomycin)
3. Resistance to individual second line drugs
4. XDR-TB test (INH, RIF, and key second line drugs)

Finally, because the genetic module leading to SML synthesis (for RRPs: the recombinase and the cognate recombination consensus sequence) are transferable to any virus, either DNA or RNA-based, the SML-phage technology of the present invention can be used to detect drug resistance in any cell infected by a virus.

Example 4

The Simultaneous Use of Multiple SML-Phage to Determine which Viable Pathogenic Bacteria is in a Clinical Sample and which Antibiotic Will Kill it in Order for the Physician to Initiate Proper Treatment Because SML-phage technology is transferable to any virus, multiple phages, each specific for a different geni or species of clinically relevant pathogen, can be generated. Each of these phage can synthesize either identical or unique SMLs and be incorporated into a device or system similar to the ones described here to generate a rapid biological AST that can be analyzed using established NAA and detection technologies. In other words, the full gamut of AST devices proposed for Mtb in this application could also be generated for any other bacteria, so long as SML technology is transferable to a virus that infects the bacteria of interest.

Another application, which is not readily obvious, is to combine several SML-phage together into one infection vessel. Each SML-phage infects a different geni or species of bacteria and generates an identical SML after infection of a viable host cell. A device could be constructed that allows for a single clinical sample to be split evenly between several reaction chambers. Each chamber contains all of the phage but a different anti-microbial. This allows the physician to analyze the clinical sample in order to answer two very important questions:

1. Which viable pathogenic bacteria is present in the sample?
2. Which antimicrobial will kill it and should therefore be prescribed to the patient?

FIG. 9 illustrates how such a system would be organized. There are various permutations upon this theme to increase specificity. For example, each geni or species specific phage would generate a unique SML. A complete diagnostic result would include detection of both a positive species identification as well as the species-specific SML-phage SML so that there would be redundancy in the analysis to ensure accuracy. Also, several antimicrobials could be added to one vessel so that a cocktail of drugs could be prescribed for extra confidence in successful treatment.

Example 5

Use of Bacteriophage Transcriptional Regulatory Mechanisms for Detecting "Naturally Occurring" SMLs This example illustrates transcriptional regulatory mechanism in bacteriophage that can be used to detect "naturally occurring" SMLs.

Many viruses exert temporal control over their gene expression programs. In other words, various functions exist to allow some genes to be expressed earlier in the infection than others and vice versa. Termination/anti-termination of phage transcription is a common mechanism to regulate the temporal expression of some genes. In this example, the mechanism is illustrated. In this example, all promoters are actively transcribed during the early phase of phage infection. For Gene A and Gene B, under control of their respective promoter, a mRNA transcript is synthesized, but a hairpin loop forms in the growing RNA polymer that destabilizes the transcription complex and leads to termination of the mRNA before it can fully transcribe, for example, Gene A as well as Gene B. However, as infection proceeds, transcription and translation of another gene, the anti-terminator, occurs relatively unimpeded. Accumulation of the anti-terminator polypeptide complex proceeds over time until it is able to bind the hairpin RNA of the transcript initiated at the promoter for Genes A and B. This polypeptide-RNA complex facilitates efficient elongation of the mRNA and transcription of the downstream, previously untranscribed, genes (e.g. GeneB). Because transcription of Gene B is dependent on the prior expression and synthesis of the anti-terminator, Gene B should not be transcribed during infection of non-viable cells or cells that have been exposed to an anti-microbial or other compound that inhibits cell viability and/or metabolism. Gene B, therefore, is an example of a "naturally occurring SML" in that decreases in cell viability through, for example, treatment of susceptible cells with an effective drug precludes or limits the transcription of Gene B and no exogenous functions need be engineered into the virus to generate an SML. Thus, detection via RNA-based NAA and detection technologies of Gene B anti-terminator regulated transcription serves as a surrogate resistance locus in a manner similar to that illustrated in Example 2.

Detection of any instance or mechanism of temporal regulation of phage transcription that reports on the drug susceptibility or viability of the cell can constitute detection of a SML or like viability locus.

Example 6

Generation of Flp Recombinase Encoding Mycobacteriophage and FRT Encoding Mycobacteriophage For initial proof of principle experiments, the SML is separated from the recombinase in order to absolutely preclude spurious generation of the SML during growth of phage stocks. Flp mediate inversion of the kanamycin resistance (KanR) cassette (i.e., generation of the SML) is then measured during co-infection of mycobacterial cells with phMM-002 and phMM-003 (FIG. 11A). Three new phasmids were created. A phasmid is a circular DNA molecule that can replicate in *E. coli* and is maintained via antibiotic selection (not shown). phMM-001 was derived directly from phAE142 bacteriophage DNA by intramolecular ligation with T4 DNA ligase followed by transformation into *E. coli* DH10B cells. phMM-002 and phMM-003 were created by electroporating linear PCR products into *E. coli* cells harboring phMM-001 and a separate plasmid expressing the red recombination system from enterobacteria phage which directs homologous recombination of the PCR product into the phMM-001 DNA. The 5' and 3' ends of the PCR products contained 42 nucleotides of DNA homologous to the DNA sequences immediately 5' and 3' of the luciferase gene in order to direct homologous recombination to replace the luciferase open reading frame with the linear PCR product. The PCR products also encoded the KanR cassette to allow for selection of recombinants on kanamycin containing agar. For phMM-002, the linear PCR product encoded the KanR cassette flanked by inverted FRT repeats. The FRT sequence is the consensus DNA binding and recombination site for the Flp recombinase. Inverted FRT repeats mediate inversion of the intervening DNA sequence in the presence of active Flp recombinase. Inversion of this sequence by Flp recombinase constitutes generation of the SML. For phMM-003, the linear PCR product encoded the Flp recombinase adjacent to the KanR cassette for selection of recombinants. In phMM-003, the Flp recombinase open reading frame is under direct transcriptional control of the robust $P_{left}$ promoter (grey star) from mycobacteriophage L5. This promoter also transcribes through the FRT flanked KanR cassette locus, although the KanR open reading frame is encoded on the opposite strand and the KanR polypeptide is not synthesized by translation of $P_{left}$ transcribed RNA. Transcription on the lower strand by $P_{left}$ in phMM-002 allows both RNA as well as DNA-based NAA methods to be used to detect the Flp mediated KanR inversion (i.e. SML generation). P1 and P2 indicate the location and direction of priming of the PCR primer pair used to verify proper, site-specific recombination of the respective PCR products into phMM-001 to create phasmids phMM-002 and phMM-003.

(FIG. 11B) Primers P1 and P2 were used to verify the proper integration of the appropriate PCR products encoding the appropriate functions for phMM-002 and phMM-003. For phMM-001, phMM-002, and phMM-003, individual colonies of *E. coli* exhibiting the correct antibiotic resistance profile were added to a PCR tube containing the appropriate buffers, Taq enzyme, and primers P1 and P2. Purified DNA from phAE142 was used as a control. PCR was performed for 25 cycles and 10% of the reaction volume was loaded onto a 1% Agaraose/TAE gel impregnated with 1 microgram/ml ethidium bromide. DNA size markers were also loaded onto the gel, which was run at 80 volts for 45 minutes followed by visualization in ultraviolet light. All isolates for each phasmid produced PCR products exhibiting the same migration through the agarose gel and were of the expected size.

We claim:

1. A method for determining the susceptibility of a microbe to a drug comprising;
    exposing a test sample to a drug composition;
    incubating the test sample with a vector, wherein the vector comprises a nucleic acid sequence encoding a polypeptide, wherein the polypeptide generates a surrogate marker locus after translation of the polypeptide; and
    detecting the presence of the surrogate marker locus using a nucleic acid detection method, wherein detection of the surrogate marker locus indicates that the microbe is resistant to the drug composition.

2. The method of claim 1, wherein the surrogate marker locus comprises a nucleic acid.

3. The method of claim 1, wherein the polypeptide is selected from one or more of the following; DNA recombinase, RNA recombinase, RNA polymerase, DNA polymerase, transcription factors, sigma factors, DNA methylases, DNA demethylases, DNA restriction endonucleases, DNA ligases, RNA ligases, histone acetylases, histone deacetylases, and uridine deaminases.

4. The method of claim 3, wherein the polypeptide is a DNA polymerase or RNA polymerase.

5. The method of claim 3, wherein the polypeptide is a DNA or RNA recombinase.

6. The method of claim 2, wherein the surrogate marker locus consists of a nucleic acid.

7. The method of claim 1, wherein the vector is a bacteriophage.

8. The method of claim 1, wherein the microbe is selected from one or more of the following; staphylococcus, streptococcaceae, neisseriaaceae, cocci, enterobacteriaceae, pseudomonadaceae, vibrionaceae, campylobacter, pasteurellaceae, bodetella, francisella, brucella, legionellaceae, bacteroidaceae, gram-negative bacilli, clostridium, corynebacterium, propionibacterium, gram-positive bacilli, anthrax, actinomyces, nocardia, mycobacterium, *Helicobacter pylori*, *Streptococcus pneumoniae*, *Candida albicans*, treponema, borrelia, leptospira, mycoplasma, ureaplasma, rickettsia, chlamydiae, systemic mycoses, opportunistic mycoses, protozoa, nematodes, trematodes, and cestodes.

9. The method of claim 1, wherein the microbe is mycobacterium.

10. The method of claim 9, wherein the mycobacterium is selected from one of the following; *M. tuberculosis, M avium-intracellulare, M. kansasii, M. fortuitum, M. chelonae, M. leprae, M. africanum, M. microti, M. avium paratuberculosis, M. intracellulare, M. scrofulaceum, M. xenopi, M. marinum*, or *M. ulcerans*.

11. The method of claim 1, wherein the sample is a body fluid sample, an industrial sample, or environmental samples.

12. The method of claim 1, wherein the drug composition comprises one or more of the following; antibiotics, isoniazid, rifampicin, ethambutol, pyrazinamide, streptomycin, clofazimine, rifabutin, fluoroquinolones ofloxacin and sparfloxacin, azithromycin, clarithromycin, dapsone, tetracycline, ciprofloxacin, doxycycline, erythromycin, ampicillin, amphotericin B, ketoconazole, fluconazole, pyrimethamine, sulfadiazine, clindamycin, azithromycin, atovaquone, pentamidine, paromomycin, diclazaril, acyclovir, trifluorouridine and type 2 antiviral nucleoside analogs, foscornat, foscarnet, ganciclovir, azidothymidine (AZT), dideoxyinosine (DDI), zalcitabine (DDC), viral protease inhibitors, peptides, antisense oligonucleotides, triplex nucleic acid sequences and ribavirin.

13. The method of claim 12, wherein the drug composition comprises on or more of the following; rifampicin, isoniazid, pyrazinamide, moxifloxacin and ethambutol or analogues thereof.

14. The method of claim 2, wherein the surrogate marker locus comprises a nucleic acid sequence derived from the vector.

15. The method of claim 2, wherein the surrogate marker locus comprises a nucleic acid sequence derived from the microbe.

16. The method of claim 11, wherein the body fluid sample is selected from the following; sputum, tears, saliva, sweat, mucus, serum, urine, and blood.

17. The method of claim 11, wherein the sample is sputum.

18. The method of claim 11, wherein the environmental sample is a sample taken from the following; drinking water, a natural body of water, community water reservoirs, recreational waters, swimming pools, whirlpools, hot tubs, spas, and water parks.

19. The method of claim 18, wherein the natural body of water is a fresh water body or a marine water body.

20. The method of claim 11, wherein the industrial sample is selected from; chemical reagents, culture media, innocula, and cleaning solutions.

21. The method of claim 1, wherein incubating the sample with a vector further comprises the application of electric pulsing, electroporation, or osmotic shock.

22. The method of claim 1, wherein the method further comprises incubating a control sample with the vector.

23. The method of claim 1, wherein the vector is a nucleic acid.

24. The method of claim 1, wherein incubating the test sample comprises incubating the test sample with multiple vectors.

25. The method of claim 24, wherein each vector comprises a nucleic acid sequence encoding a distinct polypeptide.

26. The method of claim 24, wherein each vector generates a distinct surrogate marker locus.

27. The method of claim 1, wherein the nucleic acid detection method is a nucleic acid sequence based amplification (NASBA), or a transcription mediated amplification (TMA) based method.

* * * * *